United States Patent
Deng et al.

(10) Patent No.: US 11,613,735 B2
(45) Date of Patent: Mar. 28, 2023

(54) METHODS FOR REPROGRAMING NON-HEPATOCYTE CELLS INTO HEPATOCYTE CELLS

(71) Applicants: BeiHao Stem Cell and Regenerative Medicine Translational Research Institute, Guangdong (CN); Peking University, Beijing (CN); Beijing Vitalstar Biotechnology Co., Ltd., Beijing (CN)

(72) Inventors: Hongkui Deng, Beijing (CN); Yuanyuan Du, Beijing (CN); Yan Shi, Beijing (CN); Jun Jia, Beijing (CN); Jinlin Wang, Beijing (CN); Chengang Xiang, Beijing (CN); Nan Song, Beijing (CN); Jun Xu, Beijing (CN); Ming Yin, Beijing (CN)

(73) Assignees: BeiHao Stem Cell and Regenerative Medicine Translational Research Institute, Guangdong (CN); Peking University, Beijing (CN); Beijing Vitalstar Biotechnology Co., Ltd., Beijing (CN)

( * ) Notice: Subject to any disclaimer, the term of this patent is extended or adjusted under 35 U.S.C. 154(b) by 214 days.

(21) Appl. No.: 15/118,359

(22) PCT Filed: Feb. 4, 2015

(86) PCT No.: PCT/CN2015/072232
§ 371 (c)(1),
(2) Date: Aug. 11, 2016

(87) PCT Pub. No.: WO2015/120776
PCT Pub. Date: Aug. 20, 2015

(65) Prior Publication Data
US 2017/0218333 A1     Aug. 3, 2017

(30) Foreign Application Priority Data
Feb. 12, 2014 (CN) .......................... 201410048337.X

(51) Int. Cl.
*C12N 5/00* (2006.01)
*C12N 5/071* (2010.01)
*A61K 35/407* (2015.01)

(52) U.S. Cl.
CPC ............ *C12N 5/067* (2013.01); *A61K 35/407* (2013.01); *C12N 2501/40* (2013.01); *C12N 2501/60* (2013.01); *C12N 2501/606* (2013.01); *C12N 2506/13* (2013.01); *C12N 2506/1307* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 2011/0195056 A1* | 8/2011 | Pryor | ................... | C12N 5/0667 424/93.21 |
| 2011/0280844 A1* | 11/2011 | Yu | .......................... | C12N 5/067 424/93.21 |
| 2012/0196360 A1* | 8/2012 | Okita | ................... | C12N 5/0696 435/366 |
| 2012/0231490 A1 | 9/2012 | Mizuguchi | | |
| 2013/0071365 A1 | 3/2013 | Suzuki | | |
| 2014/0242595 A1* | 8/2014 | Yu | .......................... | C12N 5/067 435/6.12 |

FOREIGN PATENT DOCUMENTS

| | | |
|---|---|---|
| JP | 2013252081 | 6/2013 |
| WO | 0244321 | 1/2002 |
| WO | 2011016588 | 2/2011 |
| WO | 2011130402 | 10/2011 |
| WO | 2012058868 | 5/2012 |
| WO | 2014039768 | 3/2014 |

OTHER PUBLICATIONS

Sekiya (Nature, 475: 1-6, 2011) (Year: 2011).*
Sekiya (Nature, 475: 1-6, 2011) supplemental materials.*
Abe, et al., "N-terminal hydrophobic amino acids of activating transcription factor 5 (ATF5) protein confer interleukin 1β (IL-1β)-induced stabilization" J. Biol. Chem., 289(7):3888-900 (2014.).
Cai, et al., "Directed differentiation of human embryonic stem cells into functional hepatic cells," Hepatology, 45(5):1229-39 (2007).
Courtois, et al., "Interaction of a liver-specific nuclear factor with the fibrinogen and alpha 1-antitrypsin promoters" Science, 238(4827):688-92 (1987).

(Continued)

*Primary Examiner* — Michael C Wilson
(74) *Attorney, Agent, or Firm* — Pabst Patent Group LLP

(57) ABSTRACT

A method for inducing reprogramming of a cell of a first type which is not a non-hepatocyte (non-hepatocyte cell), into a cell with functional hepatic drug metabolizing and transporting capabilities, is disclosed. The non-hepatocyte is induced to express or overexpress hepatic fate conversion and maturation factors, cultured in somatic cell culture medium, hepatocyte cell culture medium and hepatocyte maturation medium for a sufficient period of time to convert the non-hepatocyte cell into a cell with hepatocyte-like properties. The iHeps induced according to the methods disclosed herein are functional induced hepatocytes (iHeps) in that they express I and II drug-metabolizing enzymes and phase III drug transporters and show superior drug metabolizing activity compared to iHeps obtained by prior art methods. The iHeps thus provide a cell resource for pharmaceutical applications.

17 Claims, 9 Drawing Sheets

Specification includes a Sequence Listing.

(56) References Cited

OTHER PUBLICATIONS

Dhawan, et al., "Human hepatocyte transplantation: current experience and future challenges" Nat Rev Gastroenterol Hepatol, 7:288-98 (2010).
Gebhardt, et al., "New hepatocyte in vitro systems for drug metabolism: metabolic capacity and recommendations for application in basic research and drug development, standard operation procedures" Drug Metab. Rev. 35:145-213 ( 2003).
GENBANK Accession No. NM_001290746.1 , "*Homo sapiens* activating transcription factor 5 (ATF5), transcript variant 3, mRNA" 5 pages, first appeared Mar. 19, 2014, updated Oct. 8, 2016, retrieved Dec. 12, 2016.
Gonzalez, "Regulation of hepatocyte nuclear factor 4 alpha-mediated transcription" Drug Metab. Pharmacokinet., 23(1):2-7 (2008).
Huang , et al., "Induction of functional hepatocyte-like cells from mouse fibroblast by defined factors" Nature, 475:386-9 (2011).
Martinez, et al.,"Single-stranded antisense siRNAs guide target RNA cleavage in RNAi" Cell, 110:563-74 (2002).
Ogawa, et al., "Three-dimensional culture and cAMP signaling promote the maturation of human pluripotent stem cell-derived hepatocytes" Development, 140:3285-96 (2013).
Sahi, et al., "Hepatocytes as a tool in drug metabolism, transport and safety evaluations in drug discovery" Curr. Drug Discov.Technol., 7:188-98 (2010).
Schwartzenberger, et al., "Targeted gene transfer to human hematopoietic progenitor cell lines through the c-kit receptor" Blood, 87:472-8 (1996).
Seglen, "Preparation of isolated rat liver cells" Methods Cell Biol., 13:29-83 (1976).
Sekiya and Suzuki, "Direct conversion of mouse fibroblasts to hepatocyte-like cells by defined factors" Nature, 475:390-3 (2011).
Sladeck, et al., "Liver-enriched transcription factor HNF-4 is a novel member of the steroid hormone receptor superfamily" Genes Dev., 4(12B): 2353-65 (1990).
Song, et al., "A mouse model of inducible liver injury caused by tet-on regulated urokinase for studies of hepatocyte transplantation" Am. J. Pathol., 175:1975-83 (2009).
Takebe, et al., "Vascularized and functional human liver from an iPSC-derived organ bud transplant" Nature, 499:481-4 (2013).
Vierbuchen and Wernig, "Molecular roadblocks for cellular reprogramming" Mol. Cell, 47: 827-38 (2012).
Willenbring, "A simple code for installing hepatocyte function" Cell Stem Cell, 9:89-91 (2011).
Woo, et al., "Direct and indirect contribution of human embryonic stem cell-derived hepatocyte-like cells to liver repair in mice" Gastroenterology, 142:602-11 (2012).
Zhao, et al., "Two supporting factors greatly improve the efficiency of human iPSC generation" Cell Stem Cell, 3:475-9 (2008).
Zhao, et al., "Promotion of the efficient metabolic maturation of human pluripotent stem cell-derived hepatocytes by correcting specification defects" Cell Res., 23(1):157-61 (2013).
International Search Report for corresponding PCT application PCT/CN2015/072232 dated May 11, 2015.
Ji, et al., "Cell fate conversation: Direct induction of hepatocyte-like cells from fibroblasts", J Cellular Biochem., 114(2):256-65 (2013).
Kigiso, et al., "Transdifferentiation of human fibroblasts into hepatocyte-like cells by defined transcriptional factors", Hepatology Intl, 7(3):937-44 (2013).
Extended European Search Report for corresponding European application EP15148953 dated Jun. 2, 2017.
Canadian Office Action dated Jul. 4, 2018 Canadian Patent Application No. 2,936,526.
Wilkening, Stahl, and Bader—"Comparison of Primary Human Hepatocytes and Hepatoma Cell Line HEPG2 with regard to their Biotransformation Properties"—The American Society for Pharmacology and Experimental Therapeutics, vol. 31, No. 8, DMD 31: 1035-1042—(2003).
Office Action CA (Canada) 2,939,525 dated Jun. 18, 2019.
Office Action AU (Australia) 2015218082 dated Apr. 15, 2020.
Office Action CA (Canada) 2,939,525 dated Jun. 4, 2020.

\* cited by examiner

SEQUENCE LISTING

```
<160> NUMBER OF SEQ ID NOS: 145

<210> SEQ ID NO 1
<211> LENGTH: 1893
<212> TYPE: DNA
<213> ORGANISM: artificial sequence
<220> FEATURE:
<223> OTHER INFORMATION: HNF1A

<400> SEQUENCE: 1
atggtttcta aactgagcca gctgcagacg gagctcctgg cggccctgct cgagtcaggg      60
ctgagcaaag aggcactgat ccaggcactg ggtgagccgg ggccctacct cctggctgga     120
gaaggccccc tggacaaggg ggagtcctgc ggcggcggtc gagggagct ggctgagctg      180 cccaatgggc tgggggagac tcggggctcc gaggacgaga cggacgacga tggggaagac     240
ttcacgccac ccatcctcaa agagctggag aacctcagcc ctgaggaggc ggcccaccag     300
aaagccgtgg tggagaccct tctgcaggag gacccgtggc gtgtggcgaa gatggtcaag     360
tcctacctgc agcagcacaa catcccacag cgggaggtgg tcgataccac tggcctcaac     420
cagtcccacc tgtcccaaca cctcaacaag ggcactccca tgaagacgca gaagcgggcc     480
gccctgtaca cctggtacgt ccgcaagcag cgagaggtgg cgcagcagtt cacccatgca     540
gggcagggag ggctgattga agagcccaca ggtgatgagc taccaaccaa gaagggggcgg    600 aggaaccgtt tcaagtgggg cccagcatcc cagcagatcc tgttccaggc ctatgagagg     660
cagaagaacc ctagcaagga ggagcgagag acgctagtgg aggagtgcaa tagggcggaa     720
tgcatccaga gagggggtgtc cccatcacag gcacagggc tgggctccaa cctcgtcacg    780
gaggtgcgtg tctacaactg gtttgccaac cggcgcaaag aagaagcctt ccggcacaag    840
ctggccatgg acacgtacag cgggcccccc ccagggccag gcccgggacc tgcgctgccc    900
gctcacagct cccctggcct gcctccacct gccctctccc ccagtaaggt ccacggtgtg    960
cgctatggac agcctgcgac cagtgagact gcagaagtac cctcaagcag cggcggtccc   1020
ttagtgacag tgtctacacc cctccaccaa gtgtccccca gggcctgga gcccagccac   1080
```

```
agcctgctga gtacagaagc caagctggtc tcagcagctg ggggcccccct cccccctgtc    1140 agcaccctga cagcactgca cagcttggag cagacatccc caggcctcaa ccagcagccc    1200
cagaacctca tcatggcctc acttcctggg gtcatgacca tcgggcctgg tgagcctgcc    1260
tccctgggtc ctacgttcac caacacaggt gcctccaccc tggtcatcgg cctggcctcc    1320
acgcaggcac agagtgtgcc ggtcatcaac agcatgggca gcagcctgac caccctgcag    1380
cccgtccagt tctcccagcc gctgcacccc tcctaccagc agccgctcat gccacctgtg    1440
cagagccatg tgacccagag ccccttcatg gccaccatgg ctcagctgca gagccccac     1500 gccctctaca gccacaagcc cgaggtggcc cagtacaccc acgggcct gctcccgcag      1560 actatgctca tcaccgacac caccaacctg agcgccctgg ccagcctcac gcccaccaag    1620
caggtcttca cctcagacac tgaggcctcc agtgagtccg ggcttcacac gccggcatct    1680
caggccacca ccctccacgt ccccagccag gaccctgccg gcatccagca cctgcagccg    1740
gcccaccggc tcagcgccag cccccacagtg tcctccagca gcctggtgct gtaccagagc    1800
tcagactcca gcaatggcca gagccacctg ctgccatcca accacagcgt catcgagacc    1860
ttcatctcca cccagatggc ctcttcctcc cag                                 1893
```

<210> SEQ ID NO 2
<211> LENGTH: 1395
<212> TYPE: DNA
<213> ORGANISM: artificial sequence
<220> FEATURE:
<223> OTHER INFORMATION: HNF6

<400> SEQUENCE: 2

```
atgaacgcgc agctgaccat ggaagcgatc ggcgagctgc acggggtgag ccatgagccg      60
gtgcccgccc ctgccgacct gctgggcggc agccccacg cgcgcagctc cgtggcgcac     120
cgcggcagcc acctgccccc cgcgcacccg cgctccatgg gcatggcgtc cctgctggac    180
ggcggcagcg gcggcggaga ttaccaccac caccaccggg cccctgagca cagcctggcc    240 ggcccccctgc atcccaccat gaccatggcc tgcgagactc ccccaggtat gagcatgccc    300
accacctaca ccaccttgac ccctctgcag ccgctgcctc ccatctccac agtctcggac    360
aagttccccc ccatcaccac cccaccaccat caccaccacc accgcagcca ccaccagcgc    420
ctggcgggca cgtgagcgg tagcttcacg ctcatgcggg atgagcgcgg gctgccctcc    480
atgaataacc tctataccccc ctaccacaag gacgtggccg gcatgggcca gagcctctcg    540
cccctctcca gctccggtct gggcagcatc cacaactccc agcaagggct cccccactat    600
gcccacccgg ggggccgccat gcccaccgac aagatgctca cccccaacgg cttcgaagcc    660
caccacccgg ccatgctcgg ccgcacgggg gagcagcacc tcacgcccac ctcggccggc    720
atggtgccca tcaacggcct tcctccgcac catccccacg cccacctgaa cgcccagggc    780
cacgggcaac tcctgggcac agcccggag cccaaccctt cggtgaccgg cgcgcaggtc    840
agcaatggaa gtaattcagg gcagatggaa gagatcaata ccaaagaggt ggcgcagcgt    900
atcaccaccg agctcaagcg ctacagcatc ccacaggcca tcttcgcgca gagggtgctc    960
tgccgctccc aggggaccct ctcggacctg ctgcgcaacc ccaaaccctg gagcaaactc    1020
aaatccggcc gggagacctt ccggaggatg tggaagtggc tgcaggagcc ggagttccag    1080
cgcatgtccg cgctccgctt agcagcatgc aaaaggaaag aacaagaaca tgggaaggat    1140
agaggcaaca cacccaaaaa gcccaggttg gtcttcacag atgtccagcg tcgaactcta    1200
```

| | |
|---|---:|
| catgcaatat tcaaggaaaa taagcgtcca tccaagaat tgcaaatcac catttcccag | 1260 |
| cagctggggt tggagctgag cactgtcagc aacttcttca tgaacgcaag aaggaggagt | 1320 |
| ctggacaagt ggcaggacga gggcagctcc aattcaggca actcatcttc ttcatcaagc | 1380 |
| acttgtacca aagca | 1395 |

<210> SEQ ID NO 3
<211> LENGTH: 1392
<212> TYPE: DNA
<213> ORGANISM: artificial sequence
<220> FEATURE:
<223> OTHER INFORMATION: HNF4A

<400> SEQUENCE: 3

| | |
|---|---:|
| atgcgactct ccaaaaccct cgtcgacatg gacatggccg actacagtgc tgcactggac | 60 |
| ccagcctaca ccaccctgga atttgagaat gtgcaggtgt tgacgatggg caatgacacg | 120 |
| tccccatcag aaggcaccaa cctcaacgcg cccaacagcc tgggtgtcag cgccctgtgt | 180 |
| gccatctgcg gggaccgggc cacgggcaaa cactacggtg cctcgagctg tgacggctgc | 240 |
| aagggcttct ccggaggag cgtgcggaag aaccacatgt actcctgcag atttagccgg | 300 |
| cagtgcgtgg tggacaaaga caagaggaac cagtgccgct actgcaggct caagaaatgc | 360 |
| ttccgggctg gcatgaagaa ggaagccgtc cagaatgagc gggaccggat cagcactcga | 420 |
| aggtcaagct atgaggacag cagcctgccc tccatcaatg cgctcctgca ggcggaggtc | 480 |
| ctgtcccgac agatcacctc ccccgtctcc gggatcaacg cgacattcg ggcgaagaag | 540 |
| attgccagca tcgcagatgt gtgtgagtcc atgaaggagc agctgctggt tctcgttgag | 600 |
| tgggccaagt acatcccagc tttctgcgag ctccccctgg acgaccaggt ggccctgctc | 660 |
| agagcccatg ctggcgagca cctgctgctc ggagccacca gagatccat ggtgttcaag | 720 |
| gacgtgctgc tcctaggcaa tgactacatt gtccctcggc actgcccgga gctggcggag | 780 |
| atgagccggg tgtccatacg catccttgac gagctggtgc tgccctccca ggagctgcag | 840 |
| atcgatgaca atgagtatgc ctacctcaaa gccatcatct tctttgaccc agatgccaag | 900 |
| gggctgagcg atccagggaa gatcaagcgg ctgcgttccc aggtgcaggt gagcttggag | 960 |
| gactacatca acgaccgcca gtatgactcg cgtggccgct ttggagagct gctgctgctg | 1020 |
| ctgcccacct tgcagagcat cacctggcag atgatcgagc agatccagtt catcaagctc | 1080 |
| ttcggcatgg ccaagattga caacctgttg caggagatgc tgctgggagg tcccccagc | 1140 |
| gatgcacccc atgcccacca ccccctgcac cctcacctga tgcaggaaca tatgggaacc | 1200 |
| aacgtcatcg ttgccaacac aatgcccact cacctcagca acggacagat gtccacccct | 1260 |
| gagaccccac agccctcacc gccaggtggc tcagggtctg agccctataa gctcctgccg | 1320 |
| ggagccgtcg ccacaatcgt caagcccctc tctgccatcc cccagccgac catcaccaag | 1380 |
| caggaagtta tc | 1392 |

<210> SEQ ID NO 4
<211> LENGTH: 846
<212> TYPE: DNA
<213> ORGANISM: artificial sequence
<220> FEATURE:
<223> OTHER INFORMATION: ATF5

<400> SEQUENCE: 4

| | |
|---|---:|
| atgtcactcc tggcgaccct ggggctggag ctggacaggg ccctgctccc agctagtggg | 60 |
| ctgggatggc tcgtagacta tgggaaactc ccccccggccc ctgccccct ggctccctat | 120 |

-continued

```
gaggtccttg ggggagccct ggagggcggg cttccagtgg ggggagagcc cctggcaggt      180
gatggcttct ctgactggat gactgagcga gttgatttca cagctctcct ccctctggag      240
cctcccttac cccccggcac cctccccaa ccttccccaa ccccacctga cctggaagct       300
atggcctccc tcctcaagaa ggagctggaa cagatggaag acttcttcct agatgccccg      360
cccctcccac cccctcccc gccgccacta ccaccaccac cactaccacc agcccctcc        420 ctccccctgt ccctccctc ctttgacctc cccagccc ctgtcttgga tactctggac         480
ttgctggcca tctactgccg caacgaggcc gggcaggagg aagtggggat gccgcctctg      540
cccccgccca gcagcccccc tcctccttct ccacctcaac cttctcgcct ggccccctac      600
ccacatcctg ccaccacccg aggggaccgc aagcaaaaga agagagacca gaacaagtcg      660
gcggctctga ggtaccgcca gcggaagcgg gcagagggtg aggccctgga gggcgagtgc      720
caggggctgg aggcacggaa tcgcgagctg aaggaacggg cagagtccgt ggagcgcgag      780
atccagtacg tcaaggacct gctcatcgag gtttacaagg cccggagcca gaggacccgt      840
agctgc                                                                 846
```

<210> SEQ ID NO 5
<211> LENGTH: 2211
<212> TYPE: DNA
<213> ORGANISM: artificial sequence
<220> FEATURE:
<223> OTHER INFORMATION: PROX1

<400> SEQUENCE: 5

```
atgcctgacc atgacagcac agccctctta agccggcaaa ccaagaggag aagagttgac       60
attggagtga aaggacggt agggacagca tctgcatttt ttgctaaggc aagagcaacg      120 tttttttagtg ccatgaatcc ccaaggttct gagcaggatg ttgagtattc agtggtgcag    180
catgcagatg gggaaaagtc aaatgtactc cgcaagctgc tgaagagggc gaactcgtat     240
gaagatgcca tgatgccttt tccaggagca accataattt cccagctgtt gaaaaataac     300
atgaacaaaa atggtggcac ggagcccagt ttccaagcca gcggtctctc tagtacaggc     360
tccgaagtac atcaggagga tatatgcagc aactcttcaa gagacagccc cccagagtgt    420 ctttccccctt ttggcaggcc tactatgagc cagtttgata tggatcgctt atgtgatgag    480
cacctgagag caaagcgcgc ccgggttgag aatataattc ggggtatgag ccattccccc    540
agtgtggcat taaggggcaa tgaaaatgaa agagagatgg cccgcagtc tgtgagtccc     600 cgagaaagtt acagagaaaa caaacgcaag caaaagcttc cccagcagca gcaacagagt    660
ttccagcagc tggtttcagc ccgaaaagaa cagaagcgag aggagcgccg acagctgaaa    720
cagcagctga aggacatgca gaaacagctg cgccagctgc aggaaaagtt ctaccaaatc    780
tatgacagca ctgattcgga aaatgatgaa gatggtaacc tgtctgaaga cagcatgcgc    840
tcggagatcc tggatgccag ggcccaggac tctgtcggaa ggtcagataa tgagatgtgc    900
gagctagacc caggacagtt tattgaccga gctcgagccc tgatcagaga gcaggaaatg    960
gctgaaaaca gccgaagcg agaaggcaac aacaaagaaa gagaccatgg gccaaactcc      1020
ttacaaccgg aaggcaaaca tttggctgag accttgaaac aggaactgaa cactgccatg    1080
tcgcaagttg tggacactgt ggtcaaagtc ttttcggcca gccctcccg ccaggttcct     1140 caggtcttcc cacctctcca gatccccag gccagatttg cagtcaatgg ggaaaaccac    1200
aatttccaca ccgccaacca gcgcctgcag tgctttggcg acgtcatcat tccgaacccc    1260
```

```
ctggacacct tggcaatgt gcagatggcc agttccactg accagacaga agcactgccc    1320
ctggttgtcc gcaaaaactc ctctgaccag tctgcctccg gccctgccgc tggcggccac    1380
caccagcccc tgcaccagtc gcctctctct gccaccacgg gcttcaccac gtccaccttc    1440 cgccaccct tccccttcc cttgatggc tatccatttc agagcccatt aggtgctccc    1500
tccggctcct tctctggaaa agacagagcc tctcctgaat ccttagactt aactagggat    1560
accacgagtc tgaggaccaa gatgtcatct caccacctga ccaccaccc ttgttcacca    1620 gcacacccgc ccagcaccgc cgaagggctc tccttgtcgc tcataaagtc cgagtgcggc    1680
gatcttcaag atatgtctga aatatcacct tattcgggaa gtgcaatgca ggaaggattg    1740
tcacccaatc acttgaaaaa agcaaagctc atgttttttt atacccgtta tcccagctcc    1800
aatatgctga agacctactt ctccgacgta aagttcaaca gatgcattac ctctcagctc    1860
atcaagtggt ttagcaattt ccgtgagttt tactacattc agatggagaa gtacgcacgt    1920
caagccatca cgatggggt caccagtact gaagagctgt ctataaccag agactgtgag    1980
ctgtacaggg ctctgaacat gcactacaat aaagcaaatg actttgaggt tccagagaga    2040
ttcctggaag ttgctcagat cacattacgg gagttttca atgccattat cgcaggcaaa    2100
gatgttgatc cttcctggaa gaaggccata taaggtca tctgcaagct ggatagtgaa    2160
gtccctgaga ttttcaaatc cccgaactgc ctacaagagc tgcttcatga g            2211
```

<210> SEQ ID NO 6
<211> LENGTH: 1074
<212> TYPE: DNA
<213> ORGANISM: artificial sequence
<220> FEATURE:
<223> OTHER INFORMATION: CEBPA

<400> SEQUENCE: 6

```
atggagtcgg ccgacttcta cgaggcggag ccgcggcccc cgatgagcag ccacctgcag     60 agcccccgc acgcgcccag cagcgccgcc ttcggctttc ccggggcgc gggccccgcg    120 cagcctcccg ccccacctgc cgccccggag ccgctgggcg gcatctgcga gcacgagacg    180
tccatcgaca tcagcgccta catcgacccg gccgccttca cgacgagtt cctggccgac    240 ctgttccagc acagccggca gcaggagaag gccaaggcgg ccgtgggccc acgggcggc    300 ggcggcggcg gcgactttga ctacccgggc gcgcccgcgg ccccggcgg cgccgtcatg    360 cccgggggag cgcacgggcc cccgcccggc tacggctgcg cggccgccgg ctacctggac    420
ggcaggctgg agcccctgta cgagcgcgtc ggggcgccgg cgctgcggcc gctggtgatc    480
aagcaggagc ccgcgaagga ggatgaagcc aagcagctgg cgctggccgg cctcttccct    540
taccagccgc cgccgccgcc gccgccctcg caccccgcacc gcacccgcc gcccgcgcac    600 ctggccgccc cgcacctgca gttccagatc gcgcactgcg ccagaccac catgcacctg    660 cagcccggtc accccacgcc gccgcccacg ccgtgcca gccgcacccc gcgcccgcg    720 ctcggtgccg ccgcctgcc gggccctggc agcgcgctca aggggctggg cgccgcgcac    780
cccgacctcc gcgcgagtgg cggcagcggc gcgggcaagg ccaagaagtc ggtggacaag    840
aacagcaacg agtaccgggt gcggcgcgag cgcaacaaca tcgcggtgcg caagagccgc    900
gacaaggcca agcagcgcaa cgtggagacg cagcagaagg tgctggagct gaccagtgac    960 aatgaccgc tgcgcaagcg ggtggaacag ctgagccgcg aactggacac gctgcgggc    1020 atcttccgcc agctgccaga gagctccttg gtcaaggcca tgggcaactg cgcg        1074
```

```
<210> SEQ ID NO 7
<211> LENGTH: 1362
<212> TYPE: DNA
<213> ORGANISM: artificial sequence
<220> FEATURE:
<223> OTHER INFORMATION: MYC

<400> SEQUENCE: 7
ctggattttt tcgggtagt ggaaaaccag cagcctcccg cgacgatgcc cctcaacgtt      60
agcttcacca acaggaacta tgacctcgac tacgactcgg tgcagccgta tttctactgc     120
gacgaggagg agaacttcta ccagcagcag cagcagagcg agctgcagcc cccggcgccc     180
agcgaggata tctggaagaa attcgagctg ctgcccaccc cgcccctgtc ccctagccgc     240
cgctccgggc tctgctcgcc ctcctacgtt gcggtcacac ccttctccct tcggggagac     300
aacgacggcg gtggcgggag cttctccacg gccgaccagc tggagatggt gaccgagctg     360
ctgggaggag acatggtgaa ccagagtttc atctgcgacc cggacgacga gaccttcatc     420
aaaaacatca tcatccagga ctgtatgtgg agcggcttct cggccgccgc caagctcgtc     480
tcagagaagc tggcctccta ccaggctgcg cgcaaagaca gcggcagccc gaaccccgcc     540
cgcggccaca cgctctgctc cacctccagc ttgtacctgc aggatctgag cgccgccgcc     600
tcagagtgca tcgacccctc ggtggtcttc ccctaccctc tcaacgacag cagctcgccc     660
aagtcctgcg cctcgcaaga ctccagcgcc ttctctccgt cctcggattc tctgctctcc     720
tcgacggagt cctccccgca gggcagcccc gagccctgg tgctccatga ggagacaccg     780
cccaccacca gcagcgactc tgaggaggaa caagaagatg aggaagaaat cgatgttgtt     840
tctgtggaaa agaggcaggc tcctggcaaa aggtcagagt ctggatcacc ttctgctgga     900
ggccacagca aacctcctca gcccactg gtcctcaaga ggtgccacgt ctccacacat      960
cagcacaact acgcagcgcc tcctccact cggaaggact atcctgctgc caagagggtc     1020
aagttggaca gtgtcagagt cctgagacag atcagcaaca accgaaaatg caccagcccc     1080
aggtcctcgg acaccgagga gaatgtcaag aggcgaacac acaacgtctt ggagcgccag     1140
aggaggaacg agctaaaacg gagctttttt gccctgcgtg accagatccc ggagttggaa     1200
aacaatgaaa aggcccccaa ggtagttatc cttaaaaaag ccacagcata catcctgtcc     1260
gtccaagcag aggagcaaaa gctcatttct gaagaggact tgttgcggaa acgacgagaa     1320
cagttgaaac acaaacttga acagctacgg aactcttgtg cg                        1362

<210> SEQ ID NO 8
<211> LENGTH: 21
<212> TYPE: DNA
<213> ORGANISM: artificial sequence
<220> FEATURE:
<223> OTHER INFORMATION: Forward Primer

<400> SEQUENCE: 8
agcattgcct aggaacacga a                                                21

<210> SEQ ID NO 9
<211> LENGTH: 23
<212> TYPE: DNA
<213> ORGANISM: artificial sequence
<220> FEATURE:
<223> OTHER INFORMATION: Reverse Primer

<400> SEQUENCE: 9
ccccaggatc aaaagtaatc cca                                              23
```

<210> SEQ ID NO 10
<211> LENGTH: 21
<212> TYPE: DNA
<213> ORGANISM: artificial sequence
<220> FEATURE:
<223> OTHER INFORMATION: Forward Primer

<400> SEQUENCE: 10
tactccttca accacccgtt c                                              21

<210> SEQ ID NO 11
<211> LENGTH: 19
<212> TYPE: DNA
<213> ORGANISM: artificial sequence
<220> FEATURE:
<223> OTHER INFORMATION: Reverse Primer

<400> SEQUENCE: 11
gctatgccag acaaacccc                                                 19

<210> SEQ ID NO 12
<211> LENGTH: 21
<212> TYPE: DNA
<213> ORGANISM: artificial sequence
<220> FEATURE:
<223> OTHER INFORMATION: Forward Primer

<400> SEQUENCE: 12
cctacgaaca ggtgatgcac t                                              21

<210> SEQ ID NO 13
<211> LENGTH: 21
<212> TYPE: DNA
<213> ORGANISM: artificial sequence
<220> FEATURE:
<223> OTHER INFORMATION: Reverse Primer

<400> SEQUENCE: 13
gatttcttct cccttgcgtc t                                              21

<210> SEQ ID NO 14
<211> LENGTH: 20
<212> TYPE: DNA
<213> ORGANISM: artificial sequence
<220> FEATURE:
<223> OTHER INFORMATION: Forward Primer

<400> SEQUENCE: 14
cgccctacaa cttcaaccac                                                20

<210> SEQ ID NO 15
<211> LENGTH: 20
<212> TYPE: DNA
<213> ORGANISM: artificial sequence
<220> FEATURE:
<223> OTHER INFORMATION: Reverse Primer

<400> SEQUENCE: 15
gatcaggccc caagagcttc                                                20

<210> SEQ ID NO 16
<211> LENGTH: 21
<212> TYPE: DNA
<213> ORGANISM: artificial sequence
<220> FEATURE:
<223> OTHER INFORMATION: Forward Primer

```
<400> SEQUENCE: 16
gcctcttcct cccagtaacc a                                              21

<210> SEQ ID NO 17
<211> LENGTH: 20
<212> TYPE: DNA
<213> ORGANISM: artificial sequence
<220> FEATURE:
<223> OTHER INFORMATION: Reverse Primer

<400> SEQUENCE: 17
tatcccacga agcagcgaca                                                20

<210> SEQ ID NO 18
<211> LENGTH: 20
<212> TYPE: DNA
<213> ORGANISM: artificial sequence
<220> FEATURE:
<223> OTHER INFORMATION: Forward Primer

<400> SEQUENCE: 18
agaaagaggc agaccatcca                                                20

<210> SEQ ID NO 19
<211> LENGTH: 21
<212> TYPE: DNA
<213> ORGANISM: artificial sequence
<220> FEATURE:
<223> OTHER INFORMATION: Reverse Primer

<400> SEQUENCE: 19
tccctgcata ctccttgaag c                                              21

<210> SEQ ID NO 20
<211> LENGTH: 20
<212> TYPE: DNA
<213> ORGANISM: artificial sequence
<220> FEATURE:
<223> OTHER INFORMATION: Forward Primer

<400> SEQUENCE: 20
gcagctccaa ttcaggcaac                                                20

<210> SEQ ID NO 21
<211> LENGTH: 22
<212> TYPE: DNA
<213> ORGANISM: artificial sequence
<220> FEATURE:
<223> OTHER INFORMATION: Reverse Primer

<400> SEQUENCE: 21
catcatttgt cttgccaagt cg                                             22

<210> SEQ ID NO 22
<211> LENGTH: 21
<212> TYPE: DNA
<213> ORGANISM: artificial sequence
<220> FEATURE:
<223> OTHER INFORMATION: Forward Primer

<400> SEQUENCE: 22
cagatgccgg aaaacatgca a                                              21

<210> SEQ ID NO 23
```

```
<211> LENGTH: 21
<212> TYPE: DNA
<213> ORGANISM: artificial sequence
<220> FEATURE:
<223> OTHER INFORMATION: Reverse Primer

<400> SEQUENCE: 23
cttaagtcca ttggctcgga t                                              21

<210> SEQ ID NO 24
<211> LENGTH: 20
<212> TYPE: DNA
<213> ORGANISM: artificial sequence
<220> FEATURE:
<223> OTHER INFORMATION: Forward Primer

<400> SEQUENCE: 24
ggacaccacc ctcaagagcc                                                20

<210> SEQ ID NO 25
<211> LENGTH: 21
<212> TYPE: DNA
<213> ORGANISM: artificial sequence
<220> FEATURE:
<223> OTHER INFORMATION: Reverse Primer

<400> SEQUENCE: 25
gtcatgctct cgccgaacca g                                              21

<210> SEQ ID NO 26
<211> LENGTH: 23
<212> TYPE: DNA
<213> ORGANISM: artificial sequence
<220> FEATURE:
<223> OTHER INFORMATION: Forward Primer

<400> SEQUENCE: 26
attccatgcc gagtaacaga ccc                                            23

<210> SEQ ID NO 27
<211> LENGTH: 22
<212> TYPE: DNA
<213> ORGANISM: artificial sequence
<220> FEATURE:
<223> OTHER INFORMATION: Reverse Primer

<400> SEQUENCE: 27
agttgaccac ctcattcccg at                                             22

<210> SEQ ID NO 28
<211> LENGTH: 22
<212> TYPE: DNA
<213> ORGANISM: artificial sequence
<220> FEATURE:
<223> OTHER INFORMATION: Forward Primer

<400> SEQUENCE: 28
gcgattatct acccacgtcc ac                                             22

<210> SEQ ID NO 29
<211> LENGTH: 19
<212> TYPE: DNA
<213> ORGANISM: artificial sequence
<220> FEATURE:
<223> OTHER INFORMATION: Reverse Primer

<400> SEQUENCE: 29
```
acagaccatg tccgtgcta                                              19

<210> SEQ ID NO 30
<211> LENGTH: 19
<212> TYPE: DNA
<213> ORGANISM: artificial sequence
<220> FEATURE:
<223> OTHER INFORMATION: Forward Primer

<400> SEQUENCE: 30
ccgaactgcc tacaagagc                                              19

<210> SEQ ID NO 31
<211> LENGTH: 21
<212> TYPE: DNA
<213> ORGANISM: artificial sequence
<220> FEATURE:
<223> OTHER INFORMATION: Reverse Primer

<400> SEQUENCE: 31
aaggcagaaa gaaaacaacc a                                           21

<210> SEQ ID NO 32
<211> LENGTH: 21
<212> TYPE: DNA
<213> ORGANISM: artificial sequence
<220> FEATURE:
<223> OTHER INFORMATION: Forward Primer

<400> SEQUENCE: 32
tcttccagga gcgagatccc t                                           21

<210> SEQ ID NO 33
<211> LENGTH: 22
<212> TYPE: DNA
<213> ORGANISM: artificial sequence
<220> FEATURE:
<223> OTHER INFORMATION: Reverse Primer

<400> SEQUENCE: 33
tggtcatgag tccttccacg at                                          22

<210> SEQ ID NO 34
<211> LENGTH: 19
<212> TYPE: DNA
<213> ORGANISM: artificial sequence
<220> FEATURE:
<223> OTHER INFORMATION: Forward Primer

<400> SEQUENCE: 34
tgcctcctga actgcgtcc                                              19

<210> SEQ ID NO 35
<211> LENGTH: 20
<212> TYPE: DNA
<213> ORGANISM: artificial sequence
<220> FEATURE:
<223> OTHER INFORMATION: Reverse Primer

<400> SEQUENCE: 35
gctccgcctc gtagaagtcg                                             20

<210> SEQ ID NO 36
<211> LENGTH: 23
<212> TYPE: DNA

```
<213> ORGANISM: artificial sequence
<220> FEATURE:
<223> OTHER INFORMATION: Forward Primer

<400> SEQUENCE: 36
ccgtctaggt aagtttaaag ctc                                              23

<210> SEQ ID NO 37
<211> LENGTH: 19
<212> TYPE: DNA
<213> ORGANISM: artificial sequence
<220> FEATURE:
<223> OTHER INFORMATION: Reverse Primer

<400> SEQUENCE: 37
ctccgggtag tagctccac                                                   19

<210> SEQ ID NO 38
<211> LENGTH: 23
<212> TYPE: DNA
<213> ORGANISM: artificial sequence
<220> FEATURE:
<223> OTHER INFORMATION: Forward Primer

<400> SEQUENCE: 38
ccgtctaggt aagtttaaag ctc                                              23

<210> SEQ ID NO 39
<211> LENGTH: 19
<212> TYPE: DNA
<213> ORGANISM: artificial sequence
<220> FEATURE:
<223> OTHER INFORMATION: Reverse Primer

<400> SEQUENCE: 39
gtgtcattgc ccatcgtca                                                   19

<210> SEQ ID NO 40
<211> LENGTH: 23
<212> TYPE: DNA
<213> ORGANISM: artificial sequence
<220> FEATURE:
<223> OTHER INFORMATION: Forward Primer

<400> SEQUENCE: 40
ccgtctaggt aagtttaaag ctc                                              23

<210> SEQ ID NO 41
<211> LENGTH: 20
<212> TYPE: DNA
<213> ORGANISM: artificial sequence
<220> FEATURE:
<223> OTHER INFORMATION: Reverse Primer

<400> SEQUENCE: 41
ccgatcgctt ccatggtcag                                                  20

<210> SEQ ID NO 42
<211> LENGTH: 23
<212> TYPE: DNA
<213> ORGANISM: artificial sequence
<220> FEATURE:
<223> OTHER INFORMATION: Forward Primer

<400> SEQUENCE: 42
ccgtctaggt aagtttaaag ctc                                              23
```

<210> SEQ ID NO 43
<211> LENGTH: 22
<212> TYPE: DNA
<213> ORGANISM: artificial sequence
<220> FEATURE:
<223> OTHER INFORMATION: Reverse Primer

<400> SEQUENCE: 43 cgtcctttc actccaatgt ca                                                22

<210> SEQ ID NO 44
<211> LENGTH: 23
<212> TYPE: DNA
<213> ORGANISM: artificial sequence
<220> FEATURE:
<223> OTHER INFORMATION: Forward Primer

<400> SEQUENCE: 44
ccgtctaggt aagtttaaag ctc                                              23

<210> SEQ ID NO 45
<211> LENGTH: 21
<212> TYPE: DNA
<213> ORGANISM: artificial sequence
<220> FEATURE:
<223> OTHER INFORMATION: Reverse Primer

<400> SEQUENCE: 45
gtgaaatcaa ctcgctcagt c                                                21

<210> SEQ ID NO 46
<211> LENGTH: 22
<212> TYPE: DNA
<213> ORGANISM: artificial sequence
<220> FEATURE:
<223> OTHER INFORMATION: Forward Primer

<400> SEQUENCE: 46
gcacagaatc cttggtgaac ag                                               22

<210> SEQ ID NO 47
<211> LENGTH: 22
<212> TYPE: DNA
<213> ORGANISM: artificial sequence
<220> FEATURE:
<223> OTHER INFORMATION: Reverse Primer

<400> SEQUENCE: 47
atggaaggtg aatgtttcag ca                                               22

<210> SEQ ID NO 48
<211> LENGTH: 22
<212> TYPE: DNA
<213> ORGANISM: artificial sequence
<220> FEATURE:
<223> OTHER INFORMATION: Forward Primer

<400> SEQUENCE: 48
acaagaacag caacgagtac cg                                               22

<210> SEQ ID NO 49
<211> LENGTH: 21
<212> TYPE: DNA
<213> ORGANISM: artificial sequence
<220> FEATURE:

<223> OTHER INFORMATION: Reverse Primer

<400> SEQUENCE: 49
cattgtcact ggtcagctcc a                                          21

<210> SEQ ID NO 50
<211> LENGTH: 20
<212> TYPE: DNA
<213> ORGANISM: artificial sequence
<220> FEATURE:
<223> OTHER INFORMATION: Forward Primer

<400> SEQUENCE: 50
gtggctccag gatgttagga                                            20

<210> SEQ ID NO 51
<211> LENGTH: 20
<212> TYPE: DNA
<213> ORGANISM: artificial sequence
<220> FEATURE:
<223> OTHER INFORMATION: Reverse Primer

<400> SEQUENCE: 51
aggcctgagt tcatgttgct                                            20

<210> SEQ ID NO 52
<211> LENGTH: 21
<212> TYPE: DNA
<213> ORGANISM: artificial sequence
<220> FEATURE:
<223> OTHER INFORMATION: Forward Primer

<400> SEQUENCE: 52
cgactggagc agctactatg c                                          21

<210> SEQ ID NO 53
<211> LENGTH: 20
<212> TYPE: DNA
<213> ORGANISM: artificial sequence
<220> FEATURE:
<223> OTHER INFORMATION: Reverse Primer

<400> SEQUENCE: 53
tacgtgttca tgccgttcat                                            20

<210> SEQ ID NO 54
<211> LENGTH: 20
<212> TYPE: DNA
<213> ORGANISM: artificial sequence
<220> FEATURE:
<223> OTHER INFORMATION: Forward Primer

<400> SEQUENCE: 54
ctggccgagt ggagctacta                                            20

<210> SEQ ID NO 55
<211> LENGTH: 20
<212> TYPE: DNA
<213> ORGANISM: artificial sequence
<220> FEATURE:
<223> OTHER INFORMATION: Reverse Primer

<400> SEQUENCE: 55 aggggatag ggagagctta                                             20

-continued

```
<210> SEQ ID NO 56
<211> LENGTH: 20
<212> TYPE: DNA
<213> ORGANISM: artificial sequence
<220> FEATURE:
<223> OTHER INFORMATION: Forward Primer

<400> SEQUENCE: 56
ccatcctcaa agagctggag                                              20

<210> SEQ ID NO 57
<211> LENGTH: 20
<212> TYPE: DNA
<213> ORGANISM: artificial sequence
<220> FEATURE:
<223> OTHER INFORMATION: Reverse Primer

<400> SEQUENCE: 57
gtgctgctgc aggtaggact                                              20

<210> SEQ ID NO 58
<211> LENGTH: 20
<212> TYPE: DNA
<213> ORGANISM: artificial sequence
<220> FEATURE:
<223> OTHER INFORMATION: Forward Primer

<400> SEQUENCE: 58
ccaaaaccct cgtcgacatg                                              20

<210> SEQ ID NO 59
<211> LENGTH: 23
<212> TYPE: DNA
<213> ORGANISM: artificial sequence
<220> FEATURE:
<223> OTHER INFORMATION: Reverse Primer

<400> SEQUENCE: 59
ttctcaaatt ccagggtggt gta                                          23

<210> SEQ ID NO 60
<211> LENGTH: 19
<212> TYPE: DNA
<213> ORGANISM: artificial sequence
<220> FEATURE:
<223> OTHER INFORMATION: Forward Primer

<400> SEQUENCE: 60
tgtggaagtg gctgcagga                                               19

<210> SEQ ID NO 61
<211> LENGTH: 20
<212> TYPE: DNA
<213> ORGANISM: artificial sequence
<220> FEATURE:
<223> OTHER INFORMATION: Reverse Primer

<400> SEQUENCE: 61
tgtgaagacc aacctgggct                                              20

<210> SEQ ID NO 62
<211> LENGTH: 21
<212> TYPE: DNA
<213> ORGANISM: artificial sequence
<220> FEATURE:
<223> OTHER INFORMATION: Forward Primer
```

<400> SEQUENCE: 62
cgaacactct tcgccatctt c                                              21

<210> SEQ ID NO 63
<211> LENGTH: 21
<212> TYPE: DNA
<213> ORGANISM: artificial sequence
<220> FEATURE:
<223> OTHER INFORMATION: Reverse Primer

<400> SEQUENCE: 63
gttgctgacg gttgtgagct c                                              21

<210> SEQ ID NO 64
<211> LENGTH: 20
<212> TYPE: DNA
<213> ORGANISM: artificial sequence
<220> FEATURE:
<223> OTHER INFORMATION: Forward Primer

<400> SEQUENCE: 64
acagggctct gaacatgcac                                                20

<210> SEQ ID NO 65
<211> LENGTH: 20
<212> TYPE: DNA
<213> ORGANISM: artificial sequence
<220> FEATURE:
<223> OTHER INFORMATION: Reverse Primer

<400> SEQUENCE: 65
ggcattgaaa aactcccgta                                                20

<210> SEQ ID NO 66
<211> LENGTH: 20
<212> TYPE: DNA
<213> ORGANISM: artificial sequence
<220> FEATURE:
<223> OTHER INFORMATION: Forward Primer

<400> SEQUENCE: 66
cgagtgggcc aggagtagta                                                20

<210> SEQ ID NO 67
<211> LENGTH: 20
<212> TYPE: DNA
<213> ORGANISM: artificial sequence
<220> FEATURE:
<223> OTHER INFORMATION: Reverse Primer

<400> SEQUENCE: 67
cggtaaatgt ggtcgaggat                                                20

<210> SEQ ID NO 68
<211> LENGTH: 17
<212> TYPE: DNA
<213> ORGANISM: artificial sequence
<220> FEATURE:
<223> OTHER INFORMATION: Forward Primer

<400> SEQUENCE: 68
cccgacaccc caatctc                                                   17

<210> SEQ ID NO 69
<211> LENGTH: 20

```
<212> TYPE: DNA
<213> ORGANISM: artificial sequence
<220> FEATURE:
<223> OTHER INFORMATION: Reverse Primer

<400> SEQUENCE: 69
caggcgttgc acagatagtg                                              20

<210> SEQ ID NO 70
<211> LENGTH: 25
<212> TYPE: DNA
<213> ORGANISM: artificial sequence
<220> FEATURE:
<223> OTHER INFORMATION: Forward Primer

<400> SEQUENCE: 70
ccaacttcca cctcttctaa ctcag                                        25

<210> SEQ ID NO 71
<211> LENGTH: 23
<212> TYPE: DNA
<213> ORGANISM: artificial sequence
<220> FEATURE:
<223> OTHER INFORMATION: Reverse Primer

<400> SEQUENCE: 71
tcttgacccg aatacttgag ctc                                          23

<210> SEQ ID NO 72
<211> LENGTH: 20
<212> TYPE: DNA
<213> ORGANISM: artificial sequence
<220> FEATURE:
<223> OTHER INFORMATION: Forward Primer

<400> SEQUENCE: 72
ctatgaggtc cttgggggag                                              20

<210> SEQ ID NO 73
<211> LENGTH: 20
<212> TYPE: DNA
<213> ORGANISM: artificial sequence
<220> FEATURE:
<223> OTHER INFORMATION: Reverse Primer

<400> SEQUENCE: 73
ctcgctcagt catccagtca                                              20

<210> SEQ ID NO 74
<211> LENGTH: 20
<212> TYPE: DNA
<213> ORGANISM: artificial sequence
<220> FEATURE:
<223> OTHER INFORMATION: Forward Primer

<400> SEQUENCE: 74
acagttggag aaaatcggca                                              20

<210> SEQ ID NO 75
<211> LENGTH: 20
<212> TYPE: DNA
<213> ORGANISM: artificial sequence
<220> FEATURE:
<223> OTHER INFORMATION: Reverse Primer

<400> SEQUENCE: 75
```
atccgaggaa ctggtccttt                                          20

<210> SEQ ID NO 76
<211> LENGTH: 20
<212> TYPE: DNA
<213> ORGANISM: artificial sequence
<220> FEATURE:
<223> OTHER INFORMATION: Forward Primer

<400> SEQUENCE: 76
ttgatggaac cagaacaccc                                          20

<210> SEQ ID NO 77
<211> LENGTH: 20
<212> TYPE: DNA
<213> ORGANISM: artificial sequence
<220> FEATURE:
<223> OTHER INFORMATION: Reverse Primer

<400> SEQUENCE: 77
agctggacga tccagttgtt                                          20

<210> SEQ ID NO 78
<211> LENGTH: 20
<212> TYPE: DNA
<213> ORGANISM: artificial sequence
<220> FEATURE:
<223> OTHER INFORMATION: Forward Primer

<400> SEQUENCE: 78
gtgagctgga acagcaagtg                                          20

<210> SEQ ID NO 79
<211> LENGTH: 20
<212> TYPE: DNA
<213> ORGANISM: artificial sequence
<220> FEATURE:
<223> OTHER INFORMATION: Reverse Primer

<400> SEQUENCE: 79
ccaagcgctg tcttaactcc                                          20

<210> SEQ ID NO 80
<211> LENGTH: 20
<212> TYPE: DNA
<213> ORGANISM: artificial sequence
<220> FEATURE:
<223> OTHER INFORMATION: Forward Primer

<400> SEQUENCE: 80
ggtctggatg taccgactgc                                          20

<210> SEQ ID NO 81
<211> LENGTH: 20
<212> TYPE: DNA
<213> ORGANISM: artificial sequence
<220> FEATURE:
<223> OTHER INFORMATION: Reverse Primer

<400> SEQUENCE: 81
aaaattggaa tggcaccaac                                          20

<210> SEQ ID NO 82
<211> LENGTH: 20
<212> TYPE: DNA
<213> ORGANISM: artificial sequence

```
<220> FEATURE:
<223> OTHER INFORMATION: Forward Primer

<400> SEQUENCE: 82
accccatcac atagggsttt                                               20

<210> SEQ ID NO 83
<211> LENGTH: 20
<212> TYPE: DNA
<213> ORGANISM: artificial sequence
<220> FEATURE:
<223> OTHER INFORMATION: Reverse Primer

<400> SEQUENCE: 83
taatgtcagc gtcacttggc                                               20

<210> SEQ ID NO 84
<211> LENGTH: 20
<212> TYPE: DNA
<213> ORGANISM: artificial sequence
<220> FEATURE:
<223> OTHER INFORMATION: Forward Primer

<400> SEQUENCE: 84
ttgcccatcg aggaccagat                                               20

<210> SEQ ID NO 85
<211> LENGTH: 20
<212> TYPE: DNA
<213> ORGANISM: artificial sequence
<220> FEATURE:
<223> OTHER INFORMATION: Reverse Primer

<400> SEQUENCE: 85
gtctccgcgt tgaacactgt                                               20

<210> SEQ ID NO 86
<211> LENGTH: 18
<212> TYPE: DNA
<213> ORGANISM: artificial sequence
<220> FEATURE:
<223> OTHER INFORMATION: Forward Primer

<400> SEQUENCE: 86
gtcccacctg cccctttg                                                 18

<210> SEQ ID NO 87
<211> LENGTH: 20
<212> TYPE: DNA
<213> ORGANISM: artificial sequence
<220> FEATURE:
<223> OTHER INFORMATION: Reverse Primer

<400> SEQUENCE: 87
agtggcgcct ctgagtcttg                                               20

<210> SEQ ID NO 88
<211> LENGTH: 23
<212> TYPE: DNA
<213> ORGANISM: artificial sequence
<220> FEATURE:
<223> OTHER INFORMATION: Forward Primer

<400> SEQUENCE: 88
caggatttca gactttggac cat                                           23
```

```
<210> SEQ ID NO 89
<211> LENGTH: 20
<212> TYPE: DNA
<213> ORGANISM: artificial sequence
<220> FEATURE:
<223> OTHER INFORMATION: Reverse Primer

<400> SEQUENCE: 89
cttcaaccgc agacccttc                                                  20

<210> SEQ ID NO 90
<211> LENGTH: 21
<212> TYPE: DNA
<213> ORGANISM: artificial sequence
<220> FEATURE:
<223> OTHER INFORMATION: Forward Primer

<400> SEQUENCE: 90
agagatttcg caatccatcg g                                               21

<210> SEQ ID NO 91
<211> LENGTH: 23
<212> TYPE: DNA
<213> ORGANISM: artificial sequence
<220> FEATURE:
<223> OTHER INFORMATION: Reverse Primer

<400> SEQUENCE: 91
actggtattc cgtaaagcca aag                                             23

<210> SEQ ID NO 92
<211> LENGTH: 19
<212> TYPE: DNA
<213> ORGANISM: artificial sequence
<220> FEATURE:
<223> OTHER INFORMATION: Forward Primer

<400> SEQUENCE: 92
acatcaccta cgccagtcg                                                  19

<210> SEQ ID NO 93
<211> LENGTH: 22
<212> TYPE: DNA
<213> ORGANISM: artificial sequence
<220> FEATURE:
<223> OTHER INFORMATION: Reverse Primer

<400> SEQUENCE: 93
cgcttggaag gatttgactt ga                                              22

<210> SEQ ID NO 94
<211> LENGTH: 22
<212> TYPE: DNA
<213> ORGANISM: artificial sequence
<220> FEATURE:
<223> OTHER INFORMATION: Forward Primer

<400> SEQUENCE: 94
tactgtcggt ttcagaaatg cc                                              22

<210> SEQ ID NO 95
<211> LENGTH: 21
<212> TYPE: DNA
<213> ORGANISM: artificial sequence
<220> FEATURE:
<223> OTHER INFORMATION: Reverse Primer
```

<400> SEQUENCE: 95
gtcagcggac tctggattca g                                              21

<210> SEQ ID NO 96
<211> LENGTH: 21
<212> TYPE: DNA
<213> ORGANISM: artificial sequence
<220> FEATURE:
<223> OTHER INFORMATION: Forward Primer

<400> SEQUENCE: 96
gtgatccacg acatcgagac a                                              21

<210> SEQ ID NO 97
<211> LENGTH: 21
<212> TYPE: DNA
<213> ORGANISM: artificial sequence
<220> FEATURE:
<223> OTHER INFORMATION: Reverse Primer

<400> SEQUENCE: 97
tgcacgctga tctccttgta g                                              21

<210> SEQ ID NO 98
<211> LENGTH: 22
<212> TYPE: DNA
<213> ORGANISM: artificial sequence
<220> FEATURE:
<223> OTHER INFORMATION: Forward Primer

<400> SEQUENCE: 98
ccttcagaac ccacagagat cc                                             22

<210> SEQ ID NO 99
<211> LENGTH: 19
<212> TYPE: DNA
<213> ORGANISM: artificial sequence
<220> FEATURE:
<223> OTHER INFORMATION: Reverse Primer

<400> SEQUENCE: 99
acgctgcata gctcgttcc                                                 19

<210> SEQ ID NO 100
<211> LENGTH: 23
<212> TYPE: DNA
<213> ORGANISM: artificial sequence
<220> FEATURE:
<223> OTHER INFORMATION: Forward Primer

<400> SEQUENCE: 100
tctccaatct ggatctgagt gaa                                            23

<210> SEQ ID NO 101
<211> LENGTH: 21
<212> TYPE: DNA
<213> ORGANISM: artificial sequence
<220> FEATURE:
<223> OTHER INFORMATION: Reverse Primer

<400> SEQUENCE: 101
acagctctag ggtcacagaa g                                              21

<210> SEQ ID NO 102

```
<211> LENGTH: 21
<212> TYPE: DNA
<213> ORGANISM: artificial sequence
<220> FEATURE:
<223> OTHER INFORMATION: Forward Primer

<400> SEQUENCE: 102
ccaacggtgg caatgtgaaa t                                              21

<210> SEQ ID NO 103
<211> LENGTH: 23
<212> TYPE: DNA
<213> ORGANISM: artificial sequence
<220> FEATURE:
<223> OTHER INFORMATION: Reverse Primer

<400> SEQUENCE: 103
ccaaggactc tcattcgtct ctt                                            23

<210> SEQ ID NO 104
<211> LENGTH: 21
<212> TYPE: DNA
<213> ORGANISM: artificial sequence
<220> FEATURE:
<223> OTHER INFORMATION: Forward Primer

<400> SEQUENCE: 104
ctgaccaccc tccggaacta t                                              21

<210> SEQ ID NO 105
<211> LENGTH: 20
<212> TYPE: DNA
<213> ORGANISM: artificial sequence
<220> FEATURE:
<223> OTHER INFORMATION: Reverse Primer

<400> SEQUENCE: 105
ggccttgggt cttcctgagt                                                20

<210> SEQ ID NO 106
<211> LENGTH: 21
<212> TYPE: DNA
<213> ORGANISM: artificial sequence
<220> FEATURE:
<223> OTHER INFORMATION: Forward Primer

<400> SEQUENCE: 106
gtgtccaaca ggagatcgac g                                              21

<210> SEQ ID NO 107
<211> LENGTH: 21
<212> TYPE: DNA
<213> ORGANISM: artificial sequence
<220> FEATURE:
<223> OTHER INFORMATION: Reverse Primer

<400> SEQUENCE: 107
cacctcatga atcacggcag t                                              21

<210> SEQ ID NO 108
<211> LENGTH: 21
<212> TYPE: DNA
<213> ORGANISM: artificial sequence
<220> FEATURE:
<223> OTHER INFORMATION: Forward Primer

<400> SEQUENCE: 108
```
gaagaggagc attgaggacc g                                              21

<210> SEQ ID NO 109
<211> LENGTH: 20
<212> TYPE: DNA
<213> ORGANISM: artificial sequence
<220> FEATURE:
<223> OTHER INFORMATION: Reverse Primer

<400> SEQUENCE: 109
gcccaggatg aaagtgggat                                                20

<210> SEQ ID NO 110
<211> LENGTH: 21
<212> TYPE: DNA
<213> ORGANISM: artificial sequence
<220> FEATURE:
<223> OTHER INFORMATION: Forward Primer

<400> SEQUENCE: 110
gccacatgcc ctacacagat g                                              21

<210> SEQ ID NO 111
<211> LENGTH: 23
<212> TYPE: DNA
<213> ORGANISM: artificial sequence
<220> FEATURE:
<223> OTHER INFORMATION: Reverse Primer

<400> SEQUENCE: 111
taatgtcaca ggtcactgca tgg                                            23

<210> SEQ ID NO 112
<211> LENGTH: 20
<212> TYPE: DNA
<213> ORGANISM: artificial sequence
<220> FEATURE:
<223> OTHER INFORMATION: Forward Primer

<400> SEQUENCE: 112
cttcgtaaac cagtggcagg                                                20

<210> SEQ ID NO 113
<211> LENGTH: 20
<212> TYPE: DNA
<213> ORGANISM: artificial sequence
<220> FEATURE:
<223> OTHER INFORMATION: Reverse Primer

<400> SEQUENCE: 113
agggcttgtt aatggcagtg                                                20

<210> SEQ ID NO 114
<211> LENGTH: 20
<212> TYPE: DNA
<213> ORGANISM: artificial sequence
<220> FEATURE:
<223> OTHER INFORMATION: Forward Primer

<400> SEQUENCE: 114
agcctggtgc tcctctatct                                                20

<210> SEQ ID NO 115
<211> LENGTH: 20
<212> TYPE: DNA

<213> ORGANISM: artificial sequence
<220> FEATURE:
<223> OTHER INFORMATION: Reverse Primer

<400> SEQUENCE: 115
cccttatggt aggacaaaat                                               20

<210> SEQ ID NO 116
<211> LENGTH: 21
<212> TYPE: DNA
<213> ORGANISM: artificial sequence
<220> FEATURE:
<223> OTHER INFORMATION: Forward Primer

<400> SEQUENCE: 116
ccggggatat ggtgtgatct t                                             21

<210> SEQ ID NO 117
<211> LENGTH: 21
<212> TYPE: DNA
<213> ORGANISM: artificial sequence
<220> FEATURE:
<223> OTHER INFORMATION: Reverse Primer

<400> SEQUENCE: 117
ccgaagtccc tcatagtggt c                                             21

<210> SEQ ID NO 118
<211> LENGTH: 20
<212> TYPE: DNA
<213> ORGANISM: artificial sequence
<220> FEATURE:
<223> OTHER INFORMATION: Forward Primer

<400> SEQUENCE: 118
gagttcctgt cactgttgcg                                               20

<210> SEQ ID NO 119
<211> LENGTH: 20
<212> TYPE: DNA
<213> ORGANISM: artificial sequence
<220> FEATURE:
<223> OTHER INFORMATION: Reverse Primer

<400> SEQUENCE: 119
gtcctggcag gtgtttcatc                                               20

<210> SEQ ID NO 120
<211> LENGTH: 20
<212> TYPE: DNA
<213> ORGANISM: artificial sequence
<220> FEATURE:
<223> OTHER INFORMATION: Forward Primer

<400> SEQUENCE: 120
ccatcatgcc caatatggtt                                               20

<210> SEQ ID NO 121
<211> LENGTH: 20
<212> TYPE: DNA
<213> ORGANISM: artificial sequence
<220> FEATURE:
<223> OTHER INFORMATION: Reverse Primer

<400> SEQUENCE: 121
ccacaattcc atgttctcca                                               20

```
<210> SEQ ID NO 122
<211> LENGTH: 20
<212> TYPE: DNA
<213> ORGANISM: artificial sequence
<220> FEATURE:
<223> OTHER INFORMATION: Forward Primer

<400> SEQUENCE: 122
gccaacagga agccactatc                                          20

<210> SEQ ID NO 123
<211> LENGTH: 20
<212> TYPE: DNA
<213> ORGANISM: artificial sequence
<220> FEATURE:
<223> OTHER INFORMATION: Reverse Primer

<400> SEQUENCE: 123
cagcaattgc catagctttc                                          20

<210> SEQ ID NO 124
<211> LENGTH: 20
<212> TYPE: DNA
<213> ORGANISM: artificial sequence
<220> FEATURE:
<223> OTHER INFORMATION: Forward Primer

<400> SEQUENCE: 124
aacgggaagc cactatctca                                          20

<210> SEQ ID NO 125
<211> LENGTH: 21
<212> TYPE: DNA
<213> ORGANISM: artificial sequence
<220> FEATURE:
<223> OTHER INFORMATION: Reverse Primer

<400> SEQUENCE: 125
tcagcaattg ccatagcttt c                                        21

<210> SEQ ID NO 126
<211> LENGTH: 20
<212> TYPE: DNA
<213> ORGANISM: artificial sequence
<220> FEATURE:
<223> OTHER INFORMATION: Forward Primer

<400> SEQUENCE: 126
aatttcctaa aggccggtca                                          20

<210> SEQ ID NO 127
<211> LENGTH: 21
<212> TYPE: DNA
<213> ORGANISM: artificial sequence
<220> FEATURE:
<223> OTHER INFORMATION: Reverse Primer

<400> SEQUENCE: 127
ttgatcccaa agagaaaacc a                                        21

<210> SEQ ID NO 128
<211> LENGTH: 20
<212> TYPE: DNA
<213> ORGANISM: artificial sequence
<220> FEATURE:
```

<223> OTHER INFORMATION: Forward Primer

<400> SEQUENCE: 128
actatcccaa acccgtgatg                                                     20

<210> SEQ ID NO 129
<211> LENGTH: 21
<212> TYPE: DNA
<213> ORGANISM: artificial sequence
<220> FEATURE:
<223> OTHER INFORMATION: Reverse Primer

<400> SEQUENCE: 129
accacaattc catgttctcc a                                                   21

<210> SEQ ID NO 130
<211> LENGTH: 20
<212> TYPE: DNA
<213> ORGANISM: artificial sequence
<220> FEATURE:
<223> OTHER INFORMATION: Forward Primer

<400> SEQUENCE: 130
aacgtaattg catcagccct                                                     20

<210> SEQ ID NO 131
<211> LENGTH: 20
<212> TYPE: DNA
<213> ORGANISM: artificial sequence
<220> FEATURE:
<223> OTHER INFORMATION: Reverse Primer

<400> SEQUENCE: 131
ggtcattctg gggtatccac                                                     20

<210> SEQ ID NO 132
<211> LENGTH: 20
<212> TYPE: DNA
<213> ORGANISM: artificial sequence
<220> FEATURE:
<223> OTHER INFORMATION: Forward Primer

<400> SEQUENCE: 132
gttttctctg gggtcgatga                                                     20

<210> SEQ ID NO 133
<211> LENGTH: 20
<212> TYPE: DNA
<213> ORGANISM: artificial sequence
<220> FEATURE:
<223> OTHER INFORMATION: Reverse Primer

<400> SEQUENCE: 133
atttggcttc ttgccatcaa                                                     20

<210> SEQ ID NO 134
<211> LENGTH: 20
<212> TYPE: DNA
<213> ORGANISM: artificial sequence
<220> FEATURE:
<223> OTHER INFORMATION: Forward Primer

<400> SEQUENCE: 134
cagcctagtt cctggttgct                                                     20

```
<210> SEQ ID NO 135
<211> LENGTH: 20
<212> TYPE: DNA
<213> ORGANISM: artificial sequence
<220> FEATURE:
<223> OTHER INFORMATION: Reverse Primer

<400> SEQUENCE: 135
ggatctggtg ctcaagaatg                                          20

<210> SEQ ID NO 136
<211> LENGTH: 20
<212> TYPE: DNA
<213> ORGANISM: artificial sequence
<220> FEATURE:
<223> OTHER INFORMATION: Forward Primer

<400> SEQUENCE: 136
ctgagatcct gagcctttgg                                          20

<210> SEQ ID NO 137
<211> LENGTH: 20
<212> TYPE: DNA
<213> ORGANISM: artificial sequence
<220> FEATURE:
<223> OTHER INFORMATION: Reverse Primer

<400> SEQUENCE: 137
aagccattgg tgtttccttg                                          20

<210> SEQ ID NO 138
<211> LENGTH: 22
<212> TYPE: DNA
<213> ORGANISM: artificial sequence
<220> FEATURE:
<223> OTHER INFORMATION: Forward Primer

<400> SEQUENCE: 138
ttcaatcatg gaccaaaatc aa                                       22

<210> SEQ ID NO 139
<211> LENGTH: 20
<212> TYPE: DNA
<213> ORGANISM: artificial sequence
<220> FEATURE:
<223> OTHER INFORMATION: Reverse Primer

<400> SEQUENCE: 139
tgagtgacag agctgccaag                                          20

<210> SEQ ID NO 140
<211> LENGTH: 20
<212> TYPE: DNA
<213> ORGANISM: artificial sequence
<220> FEATURE:
<223> OTHER INFORMATION: Forward Primer

<400> SEQUENCE: 140
gaaaacaaga cgctgcaatg                                          20

<210> SEQ ID NO 141
<211> LENGTH: 24
<212> TYPE: DNA
<213> ORGANISM: artificial sequence
<220> FEATURE:
<223> OTHER INFORMATION: Reverse Primer
```

```
<400> SEQUENCE: 141
tcctttctat ttgagtgatg gaaa                                          24

<210> SEQ ID NO 142
<211> LENGTH: 19
<212> TYPE: DNA
<213> ORGANISM: artificial sequence
<220> FEATURE:
<223> OTHER INFORMATION: Forward Primer

<400> SEQUENCE: 142
agggggacat gaacctcag                                                19

<210> SEQ ID NO 143
<211> LENGTH: 20
<212> TYPE: DNA
<213> ORGANISM: artificial sequence
<220> FEATURE:
<223> OTHER INFORMATION: Reverse Primer

<400> SEQUENCE: 143
aggtccccat catagatccc                                               20

<210> SEQ ID NO 144
<211> LENGTH: 20
<212> TYPE: DNA
<213> ORGANISM: artificial sequence
<220> FEATURE:
<223> OTHER INFORMATION: Forward Primer

<400> SEQUENCE: 144
tgcaccacca actgcttagc                                               20

<210> SEQ ID NO 145
<211> LENGTH: 21
<212> TYPE: DNA
<213> ORGANISM: artificial sequence
<220> FEATURE:
<223> OTHER INFORMATION: Reverse Primer

<400> SEQUENCE: 145
ggcatggact gtggtcatga g                                             21
```

METHODS FOR REPROGRAMING NON-HEPATOCYTE CELLS INTO HEPATOCYTE CELLS

CROSS-REFERENCE TO RELATED APPLICATIONS

This application a U.S. National stage entry of PCT/CN2015/072232, filed Feb. 4, 2015, which claims benefit of Chinese Provisional Application No. 201410048337.X, filed Feb. 12, 2014, incorporated herein by reference.

REFERENCE TO SEQUENCE LISTING

The Sequence Listing submitted as a text file named "GHBCL_101_ST25_txt," created on Feb. 2, 2015, and having a size of 41,627 bytes is hereby incorporated by reference.

FIELD OF THE INVENTION

The present invention generally relates to use of hepatocyte fate conversion and maturation factors for reprogramming eukaryotic cells into hepatocyte cells.

BACKGROUND OF THE INVENTION

Functional human cell types are in high demand in the field of regenerative medicine and drug development. They show great potential for repairing or replacing diseased and damaged tissues and can be valuable tools for pharmaceutical applications. However, the application of functional human cell types in these areas is limited due to a shortage of donors (Castell et al., *Expert Opin. Drug Metab. Toxicol.* 2:183-212 (2006)). To solve this dilemma, novel strategies for generating functionally mature cells are in high demand. Recently, lineage reprogramming has emerged as an effective method for changing the fate of somatic cells (Vierbuchen and Wernig, *Mol. Cell,* 47: 827-838 (2012)). In principle, one cell type can be converted directly to the final mature state of another cell type and can bypass its intermediate states during lineage reprogramming. Consequently, functionally mature cells may be obtained using this strategy and may potentially provide a promising source of functional human cells.

Functional human hepatocytes are the most significant in vitro model for evaluating drug metabolism and are potentially widely applicable in pharmaceutical development. Because unacceptable metabolic and toxicity effects on the liver are largely responsible for the failure of new chemical entities in drug discovery (Baranczewski et al., *Pharmacol. Rep.,* 58:453-472 (2006)), it is essential to use human hepatocytes, which serve as the closest in vitro model of human liver in assays of absorption, distribution, metabolism, excretion, and toxicity (ADME/Tox), to identify compounds that display favorable pharmacokinetics (Sahi et al., *Curr. Drug Discov. Technol.,* 7:188-198 (2010)). Currently, primary human hepatocytes that are derived from individuals with different genetic backgrounds are frequently used in drug development, but the resulting diversity of genetic backgrounds hinders the reproducibility of the results obtained from pharmaceutical studies using these cells. Additionally, the scarcity of human liver donors greatly limits the use of primary human hepatocytes (Castell et al., *Expert Opin. Drug Metab. Toxicol.* 2:183-212 (2006)) and, as a result, alternative resources for human hepatocytes with a high reproducibility are urgently required for use in drug discovery.

Different strategies to generate functional hepatocytes have been studied. Human hepatocytes have been derived from human pluripotent stem cells by directed differentiation (Cai et al., *Hepatology,* 45:1229-1239 (2007); Ogawa et al., *Development,* 140:3285-3296 (2013); Takebe et al., *Nature,* 499:481-484 (2013); Zhao et al., *Cell Res.,* 23:157-161 (2013)). This strategy has progressed quickly in recent years, although the immature phenotype of the cells derived from pluripotent stem cells remains a technological obstacle. In principle, fully functional hepatocytes are relatively difficult to obtain using this method, as the whole process involves multiple key steps that affect the final stage of hepatocyte formation. In contrast, lineage reprogramming allows the lineage conversion of a somatic cell without passing through an intermediate state. Although mouse hepatocytes have been transdifferentiated from fibroblasts (Huang et al., *Nature,* 475:386-389 2011; Sekiya and Suzuki, *Nature,* 475:390-393 (2011)), these cells still express several hepatoblast markers such as α-fetoprotein (AFP) and lack the expression of several key cytochrome P450 enzymes (CYPs) that are responsible for drug metabolism, suggesting a functionally immature phenotype for these cells (Willenbring, *Cell Stem Cell,* 9:89-91 (2011)).

There is therefore a need for a method inducing non-hepatocyte cells into functional induced hepatocytes that show improved hepatocyte functional activity, when compared to known induced hepatocytes.

It is therefore an object of the present invention to provide a method of inducing conversion of a non-hepatocyte cell, into an induced hepatocyte cell (iHep) with metabolic function.

It is also an object of the present invention to provide induced hepatic cells with metabolic function.

It is still an object of the present invention to provide a method using induced hepatocytes for drug development, bioartificial liver system and in vivo and in-vitro hepatic applications.

It is further an object of the present invention to provide kits for reprogramming a non-hepatocyte into an iHep.

SUMMARY OF THE INVENTION

A method for inducing reprogramming of a cell of a first type which is not a hepatocyte (i.e., non-hepatocyte cells), into a hepatocyte-like cell, as indicated by functional hepatic drug metabolizing and transporting capabilities, is disclosed. These cells are denoted herein as induced hepatocytes (iHeps). The non-hepatocyte is treated to upregulate hepatic fate conversion and maturation factors ("collectively, "Hepatocyte inducing factors"), cultured in somatic cell culture medium (transformation phase), expanded in hepatocyte cell culture medium (expansion phase) and further cultured in hepatocyte maturation medium (maturation phase) for a sufficient period of time to convert the cell into a cell with hepatocyte-like properties.

In a preferred embodiment, the non-hepatocyte cell is transformed to overexpress at least one of the following Hepatocyte inducing factors: Hepatocyte nuclear factor 1-alpha (HNF1A), Hepatocyte nuclear factor 4-alpha (HNF4A), and Hepatocyte nuclear factor 6-alpha (HNF6), Activating transcription factor 5 (ATF5), Prospero homeobox protein 1 (PROX1), and CCAAT/enhancer-binding protein alpha (CEBPA). In some embodiments the cell is transformed to express at least 2, at least 3, at least 4 or at least 5 of the hepatocyte inducing factors. In a preferred embodiment, the cell is transformed to overexpress all 6 Hepatocyte inducing factors. In some embodiments, the method further includes upregulating MYC, and/or downregulating p53 gene expression and/or protein activity. Non-hepatocytes (treated to upregulate hepatocyte inducing factors; and optionally upregulate MYC and optionally, downregulate p53) are then expanded in vitro to obtain iHeps. In one embodiment, transfected cells are cultured in somatic cell culture medium, for example, DMEM, for a period of at least 7 days, until about 80% confluence. The cells are then replated and expanded in hepatocyte cell culture medium (HCM) for about 15 to 30 days, preferably for about 18-30 days, and more preferably, for about 18 days, following which the cells are transferred into a hepatocyte maturation medium for about 5 days. Induced hepatocytes (iHeps) are obtained following this cell culture scheme.

The cells are identified as iheps, based on known structural and functional properties of hepatocytes.

Also disclosed are functional induced hepatocytes (iHeps). In a preferred embodiment, the induced hepatocytes are human induced hepatocytes (hiHeps). iHeps express at least one hepatocyte marker selected from the group consisting of albumin, Cytochrome P450 (Cyp)3A4, CYPB6, CYP1A2, CYP2C9, and CYP2C19. In a preferred embodiment, iHeps express at least two, three or four or five or six of CYPB6, CYP3A4, CYPB6, CYP1A2, CYP2C9, and CYP2C19.

Transplanted hiHeps repopulate up to 30% of the livers of Tet-uPA/Rag2$^{-/-}$γc$^{-/-}$ mice and secrete more than 300 mg/ml human albumin in vivo. Thus human hepatocytes with drug metabolic function can be generated by lineage reprogramming, thus providing a cell resource for in vitro drug development and in vivo applications within the context of liver disease/failure.

Kits for inducing reprogramming of non-hepatocytes cells into iHeps are also disclosed. The kit includes factors which upregulate the Hepatocyte inducing factors disclosed herein, and optionally, factors which upregulate MYC and downregulate p53 gene expression and/or protein levels.

DETAILED DESCRIPTION OF THE INVENTION

I. Definitions

Figure 1A:
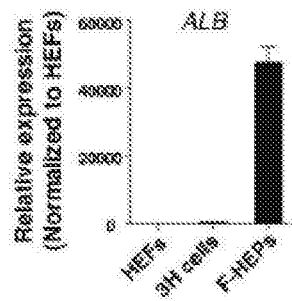
FIG. 1A is a bar graph showing gene expression analysis of ALB in F-HEPs, HEFs and 3H cells. n=2.

As used herein a "culture" means a population of cells grown in a medium and optionally passaged. A cell culture may be a primary culture (e.g., a culture that has not been passaged) or may be a secondary or subsequent culture (e.g., a population of cells which have been subcultured or passaged one or more times).

As used herein, "downregulation" or "downregulate" refers to the process by which a cell decreases the quantity and/or activity of a cellular component, for example, DNA, RNA or protein, in response to an external variable.

As used herein, "embryonic stem cell (ESC)-derived hepatocytes (ES-Heps)" refer to induced hepatocytes derived according to the methods disclosed in Zhao, et al., Cell Res., 23(1):157-161 (2013).

As used herein, "functional induced hepatocytes (iHeps)" refers to induced hepatocytes which show the activity of at least one of CYP3A4, CYP2C9, or CYP2C19, at levels 50% higher than the activity of the same enzyme in ES-Heps obtained from the same organism. The activity of the enzyme can be 55%, 60%, 65%, 70%, 75%, 80%, 85%, 90%, 95%, 100% or more, higher than the activity in ES-Heps.

As used herein, the term "host cell" refers to non-hepatocytes eukaryotic cells into which a recombinant nucleotide, such as a vector, can be introduced.

The term "induced hepatocytes" (iHeps) as used herein refers to cells which are not naturally occurring hepatocytes, and which are artificially derived from non-hepatocyte cells.

The term "isolated" or "purified" when referring to hiHEPS means chemically induced pluripotent stem cells at least 30%, 35%, 40%, 45%, 50%, 55%, 60%, 65%, 70%, 75%, 80%, 85%, 90%, 95%, or 99% free of contaminating cell types such as non-hepatocyte cells. The isolated iheps may also be substantially free of soluble, naturally occurring molecules.

The terms "oligonucleotide" and "polynucleotide" generally refer to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C As used herein, "transformed" and "transfected" encompass the introduction of a nucleic acid (e.g. a vector) into a cell by a number of techniques known in the art.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

"Reprogramming" as used herein refers to the conversion of a one specific cell type to another. For example, a cell that is not a hepatocyte cab be reprogrammed into a cell that is morphologically and functionally like a hepatocyte.

As used herein "treating a cell/cells" refers to contacting the cell(s) with factors such as the nucleic acids disclosed herein to downregulate or upregulate the quantity and/or activity of a cellular component, for example, DNA, RNA or protein. This phrase also encompasses contacting the cell(s) with any factors including proteins and small molecules that can downregulate or upregulate the gene/protein of interest.

The term "upregulate expression of" means to affect expression of, for example to induce expression or activity, or induce increased/greater expression or activity relative to an untreated cell.

As used herein, "upregulation" or "upregulate" refers to the process by which a cell increases the quantity and/or activity of a cellular component, for example, DNA, RNA or protein, in response to an external variable.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

II. Compositions

A. Factors Inducing Non-Hepatocyte Cells into Hepatocyte-Like Properties

Obtaining fully functional cell types is a major challenge for drug discovery, bioartificial liver and regenerative medicine. Currently, a fundamental solution to this key problem is still lacking. Functional human induced hepatocytes (hi-Heps) can be generated from fibroblasts by upregulating at least one factor selected from the group consisting of HNF1A, HNF4A, HNF6, ATF5, PROX1, and CEBPA, as well as MYC genes mRNA or protein levels. All known functional variants and isoforms of the hepatocyte inducing factors disclosed herein are contemplated. These known sequences are readily available in the National Center for Biotechnology Information Genebak database.

Preferably, p53 activity is additionally, downregulated as indicated by a downregulation of the p53 gene, mRNA and/or protein levels.

1. Nucleic Acids Encoding Hepatocyte Inducing Factors i. HNF1A

HNF1A (also known as TCF1) is a tumor suppressor gene involved in liver tumorigenesis. It is located on the long arm of chromosome 12, encoded by 10 exons, spanning 23 kilobases, and is expressed in various tissues, including liver, kidney, pancreas, and digestive tract. It encodes a transcription factor HNF1, which, in the liver, is implicated in hepatocyte differentiation and is required for expression of certain liver-specific genes, including albumin, β-fibrinogen, and $\alpha_1$-antitrypsin. Courtois, et al., *Science*, 30(4827: 688-692 (1987). The HNF1A gene is conserved in chimpanzee, Rhesus monkey, dog, cow, mouse, rat, chicken, zebrafish, and frog.

In a preferred embodiment, a nucleotide encoding HNF1A is represented below by SEQ ID NO:1.

```
                                          (SEQ ID NO: 1)
atggtttcta aactgagcca gctgcagacg gagctcctgg cggccctgct cgagtcaggg ctgagcaaag aggcactgat ccaggcactg ggtgagccgg ggccctacct cctggctgga gaaggccccc tggacaaggg ggagtcctgc ggcggcggtc gaggggagct ggctgagctg cccaatgggc tgggggagac tcggggctcc gaggacgaga cggacgacga tggggaagac ttcacgccac ccatcctcaa agagctggag aacctcagcc ctgaggaggc ggcccaccag aaagccgtgg tggagaccct tctgcaggag gacccgtggc gtgtggcgaa gatggtcaag tcctacctgc agcagcacaa catcccacag cgggaggtgg tcgataccac tggcctcaac cagtcccacc tgtcccaaca cctcaacaag ggcactccca tgaagacgca gaagcgggcc gccctgtaca cctggtacgt ccgcaagcag cgagaggtgg cgcagcagtt cacccatgca gggcagggag ggctgattga agagcccaca ggtgatgagc taccaaccaa gaaggggcgg aggaaccgtt tcaagtgggg cccagcatcc cagcagatcc tgttccaggc ctatgagagg cagaagaacc ctagcaagga ggagcgagag acgctagtgg aggagtgcaa tagggcggaa
```
tgcatccaga gaggggtgtc cccatcacag gcacaggggc tgggctccaa cctcgtcacg gaggtgcgtg tctacaactg gtttgccaac cggcgcaaag aagaagcctt ccggcacaag ctggccatgg acacgtacag cgggccccc ccagggccag gcccgggacc tgcgctgccc gctcacagct cccctggcct gcctccacct gccctctccc ccagtaaggt ccacggtgtg cgctatggac agcctgcgac cagtgagact gcagaagtac cctcaagcag cggcggtccc ttagtgacag tgtctacacc cctccaccaa gtgtccccca cgggcctgga gcccagccac agcctgctga gtacagaagc caagctggtc tcagcagctg ggggccccct cccccctgtc agcaccctga cagcactgca cagcttggag cagacatccc caggcctcaa ccagcagccc cagaacctca tcatggcctc acttcctggg gtcatgacca tcgggcctgg tgagcctgcc tccctgggtc ctacgttcac caacacaggt gcctccaccc tggtcatcgg cctggcctcc acgcaggcac agagtgtgcc ggtcatcaac agcatgggca gcagcctgac caccctgcag cccgtccagt tctcccagcc gctgcacccc tcctaccagc agccgctcat gccacctgtg cagagccatg tgacccagag ccccttcatg gccaccatgg ctcagctgca gagccccac gccctctaca gccacaagcc cgaggtggcc cagtacaccc acacgggcct gctcccgcag actatgctca tcaccgacac caccaacctg agcgccctgg ccagcctcac gcccaccaag caggtcttca cctcagacac tgaggcctcc agtgagtccg ggcttcacac gccggcatct caggccacca ccctccacgt ccccagccag gaccctgccg gcatccagca cctgcagccg gcccaccggc tcagcgccag ccccacagtg tcctccagca gcctggtgct gtaccagagc tcagactcca gcaatggcca gagccacctg ctgccatcca accacagcgt catcgagacc ttcatctcca cccagatggc ctcttcctcc cag A nucleic acid encoding HNF1A can include a sequence having at least 80%, 85%, 90%, 95%, 99%, or 100% sequence identity to SEQ ID NO:1 or a functional fragment or variant of SEQ ID NO:1.

A number of naturally occurring variants of nucleic acids encoding HNF1A and their activities are known in the art, and include, but are not limited to, the transcript variant for HNF1A as represented by GenBank Accession No: XM_005253931.1.

ii. HNF6

HNF6 was originally characterized as a transcriptional activator of the liver promoter of the 6-phosphofructo-2-kinase (pfk-2) gene, is expressed in liver, brain, spleen, pancreas, and testis. Lannoy, et al., *J. Biol. Chem.*, 273: 13552-13562 (1998). Alternative splicing results in multiple transcript variants.

In one embodiment, HNF6 is represented by SEQ ID NO:2.

(SEQ ID NO: 2)
atgaacgcgc agctgaccat ggaagcgatc ggcgagctgc
acggggtgag ccatgagccg gtgcccgccc ctgccgacct
gctgggcggc agcccccacg cgcgcagctc cgtggcgcac
cgcggcagcc acctgccccc cgcgcacccg cgctccatgg
gcatggcgtc cctgctggac ggcggcagcg gcggcggaga
ttaccaccac caccaccggg ccctgagca cagcctggcc
ggcccctgc atcccaccat gaccatggcc tgcagagctc
ccccaggtat gagcatgccc accacctaca ccaccttgac
ccctctgcag ccgctgcctc ccatctccac agtctcggac
aagttccccc accatcacca ccaccaccat caccaccacc
acccgcacca ccaccagcgc ctggcgggca acgtgagcgg
tagcttcacg ctcatgcggg atgagcgcg gctggcctcc
atgaataacc tctataccc ctaccacaag gacgtggccg
gcatgggcca gagcctctcg cccctctcca gctccggtct
gggcagcatc cacaactccc agcaagggct cccccactat
gcccacccgg gggccgccat gccaccgac aagatgctca
cccccaacgg cttcgaagcc caccacccgg ccatgctcgg
ccgccacggg gagcagcacc tcacgcccac ctcggccggc
atggtgccca tcaacggcct tcctccgcac catccccacg
cccacctgaa cgcccagggc cacgggcaac tcctgggcac
agcccgggag cccaaccctt cggtgaccgg cgcgcaggtc
agcaatggaa gtaattcagg gcagatggaa gagatcaata
ccaaagaggt ggcgcagcgt atcaccaccg agctcaagcg
ctacagcatc ccacaggcca tcttcgcgca gagggtgctc
tgccgctccc aggggaccct ctcggacctg ctgcgcaacc
ccaaaccctg gagcaaactc aaatccggcc gggagacctt
ccggaggatg tggaagtggc tgcaggagcc ggagttccag
cgcatgtccg cgctccgctt agcagcatgc aaaaggaaag
aacaagaaca tgggaaggat agaggcaaca cacccaaaaa
gcccaggttg gtcttcacag atgtccagcg tcgaactcta
catgcaatat tcaaggaaaa taagcgtcca tccaaagaat
tgcaaatcac catttcccag cagctggggt tggagctgag
cactgtcagc aacttcttca tgaacgcaag aaggaggagt
ctggacaagt ggcaggacga gggcagctcc aattcaggca
actcatcttc ttcatcaagc acttgtacca aagca A nucleic acid encoding HNF6 can include a sequence having at least 80%, 85%, 90%, 95%, 99%, or 100% sequence identity to SEQ ID NO:2 or a functional fragment or variant of SEQ ID NO:2.

A number of naturally occurring variants of nucleic acids encoding HNF6 and their activities are known in the art. A human hepatocyte nuclear factor 6 (HNF6) gene is described under NCBI GenBank Accession No. AF035581. A *Homo sapiens* transcript variant mRNA is disclosed under Genbank Accession No. NM_004498.2.

iii. HNF4A

Hepatocyte nuclear factor 4 alpha (HNF4alpha, NR2A1, gene symbol HNF4A) is a highly conserved member of the nuclear receptor (NR) superfamily of ligand-dependent transcription factors (Sladeck, et al., *Genes Dev.*, 4(12B): 2353-65 (1990). HNF4A1 is expressed in liver (hepatocytes), kidney, small intestine, etc. HNF4A2 is the most predominant isoform in the liver. HNF4A regulates most if not all of the apolipoprotein genes in the liver and regulates the expression of many cytochrome P450 genes (e.g., CYP3A4, CYP2D6) and Phase II enzymes and hence may play a role in drug metabolism (Gonzalez, et al., *Drug Metab. Pharmacokinet.*, 23(1):2-7 (2008).

In one embodiment, HNF4 is represented by SEQ ID NO:3.

(SEQ ID NO: 3)
atgcgactct ccaaaaccct cgtcgacatg gacatggccg
actacagtgc tgcactggac ccagcctaca ccaccctgga
atttgagaat gtgcaggtgt tgacgatggg caatgacacg
tccccatcag aaggcaccaa cctcaacgcg cccaacagcc
tgggtgtcag cgccctgtgt gccatctgcg gggaccgggc
cacgggcaaa cactacggtg cctcgagctg tgacggctgc
aagggcttct tccggaggag cgtgcggaag aaccacatgt
actcctgcag atttagccgg cagtgcgtgg tggacaaaga
caagaggaac cagtgccgct actgcaggct caagaaatgc
ttccgggctg gcatgaagaa ggaagccgtc cagaatgagc
gggaccggat cagcactcga aggtcaagct atgaggacag
cagcctgccc tccatcaatg cgctcctgca ggcggaggtc
ctgtcccgac agatcacctc ccccgtctcc gggatcaacg
gcgacattcg ggcgaagaag attgccagca tcgcagatgt
gtgtgagtcc atgaaggagc agctgctggt tctcgttgag
tgggccaagt acatcccagc ttctgcgag ctccccctgg
acgaccaggt ggccctgctc agagcccatg ctggcgagca
cctgctgctc ggagccacca agatccat ggtgttcaag
gacgtgctgc tcctaggcaa tgactacatt gtccctcggc
actgcccgga gctggcggag atgagccggg tgtccatacg
catccttgac gagctggtgc tgcccttcca ggagctgcag
atcgatgaca atgagtatgc ctacctcaaa gccatcatct
tctttgaccc agatgccaag gggctgagcg atccaggaa
gatcaagcgg ctgcgttccc aggtgcaggt gagcttggag
gactacatca acgaccgcca gtatgactcg cgtggccgct
ttggagagct gctgctgctg ctgcccacct gcagagcat
cacctggcag atgatcgagc agatccagtt catcaagctc
ttcggcatgg ccaagattga caacctgttg caggagatgc

```
tgctgggagg gtcccccagc gatgcacccc atgcccacca cccctgcac cctcacctga tgcaggaaca tatgggaacc aacgtcatcg ttgccaacac aatgccact cacctcagca acggacagat gtccaccct gagacccac agccctcacc gccaggtggc tcagggtctg agccctataa gctcctgccg ggagccgtcg ccacaatcgt caagcccctc tctgccatcc cccagccgac catcaccaag caggaagtta tc
```

A nucleic acid encoding HNF4 can include a sequence having at least 80%, 85%, 90%, 95%, 99%, or 100% sequence identity to SEQ ID NO:3 or a functional fragment or variant of SEQ ID NO:3.

A number of naturally occurring variants of nucleic acids encoding HNF4 and their activities are known in the art. A human hepatocyte nuclear factor 4 gene is described under NCBI GenBank Accession No. BC137539.1.

iv. ATF5

ATF5 encodes activating transcription factor 5. ATF5 transcripts and protein are expressed in a wide variety of tissues, in particular, high expression of transcripts in liver.

In one embodiment, ATF5 is represented by SEQ ID NO:4.

```
                                    (SEQ ID NO: 4)
atgtcactcc tggcgaccct ggggctggag ctggacaggg ccctgctccc agctagtggg ctgggatggc tcgtagacta tgggaaactc cccccggccc ctgccccct ggctccctat gaggtccttg ggggagccct ggagggcggg cttccagtgg ggggagagcc cctggcaggt gatggcttct ctgactggat gactgagcga gttgatttca cagctctcct ccctctggag cctcccttac cccccggcac cctcccccaa cctccccaa ccccacctga cctggaagct atggcctccc tcctcaagaa ggagctggaa cagatggaag acttcttcct agatgccccg cccctcccac caccctcccc gccgccacta ccaccaccac cactaccacc agcccctcc ctccccctgt ccctcccctc ctttgacctc cccagcccc ctgtcttgga tactctggac ttgctggcca tctactgccg caacgaggcc gggcaggagg aagtggggat gccgcctctg cccccgccac agcagccccc tcctccttct ccacctcaac cttctcgcct ggcccctac ccacatcctg ccaccacccg aggggaccgc aagcaaaaga agagagacca gaacaagtcg gcggctctga ggtaccgcca gcggaagcgg gcagagggtg aggcctgga gggcgagtgc caggggctgg aggcacggaa tcgcgagctg aaggaacggg cagagtccgt ggagcgcgag atccagtacg tcaaggacct gctcatcgag gtttacaagg cccggagcca gaggacccgt agctgc
```

A nucleic acid encoding ATF5 can include a sequence having at least 80%, 85%, 90%, 95%, 99%, or 100% sequence identity to SEQ ID NO:4 or a functional fragment or variant of SEQ ID NO:4. A number of naturally occurring variants of nucleic acids encoding ATF5 and their activities are known in the art. A human ATF5 transcript variant 3 (mRNA) is described under Genbank Accession No. NM_001290746.1 (Abe, et al., *J. Biol. Chem.*, 289(7):3888-3900 (2014)).

v. PROX1

In one embodiment, PROX1 is represented by SEQ ID NO:5.

```
                                    (SEQ ID NO: 5)
atgcctgacc atgacagcac agccctctta agccggcaaa ccaagaggag aagagttgac attggagtga aaaggacggt agggacagca tctgcatttt ttgctaaggc aagagcaacg tttttagtg ccatgaatcc ccaaggttct gagcaggatg ttgagtattc agtggtgcag catgcagatg gggaaaagtc aaatgtactc cgcaagctgc tgaagagggc gaactcgtat gaagatgcca tgatgccttt tccaggagca accataattt cccagctgtt gaaaaataac atgaacaaaa atggtggcac ggagcccagt ttccaagcca gcggtctctc tagtacaggc tccgaagtac atcaggagga tatatgcagc aactcttcaa gagacagccc cccagagtgt ctttcccctt ttggcaggcc tactatgagc cagtttgata tggatcgctt atgtgatgag cacctgagag caaagcgcgc ccgggttgag aatataattc ggggtatgag ccattccccc agtgtggcat taaggggcaa tgaaaatgaa agagagatgg ccccgcagtc tgtgagtccc cgagaaagtt acagagaaaa caaacgcaag caaaagcttc cccagcagca gcaacagagt ttccagcagc tggtttcagc ccgaaaagaa cagaagcgag aggagcgccg acagctgaaa cagcagctgg aggacatgca gaaacagctg cgccagctgc aggaaaagtt ctaccaaatc tatgacagca ctgattcgga aaatgatgaa gatggtaacc tgtctgaaga cagcatgcgc tcggagatcc tggatgccag ggcccaggac tctgtcggaa ggtcagataa tgagatgtgc gagctagacc caggacagtt tattgaccga gctcgagccc tgatcagaga gcaggaaatg gctgaaaaca agccgaagcg agaaggcaac aacaaagaaa gagaccatgg gccaaactcc ttacaaccgg aaggcaaaca tttggctgag accttgaaac aggaactgaa cactgccatg tcgcaagttg tggacactgt ggtcaaagtc ttttcggcca agccctcccg ccaggttcct caggtcttcc cacctctcca gatccccag gccagatttg cagtcaatgg ggaaaaccac aatttccaca ccgccaacca gcgcctgcag tgctttggcg acgtcatcat tccgaacccc ctggacacct ttggcaatgt gcagatggcc agttccactg accagacaga agcactgccc
```

-continued

```
ctggttgtcc gcaaaaactc tctctgaccag tctgcctccg gccctgccgc tggcggccac caccagcccc tgcaccagtc gcctctctct gccaccacgg gcttcaccac gtccaccttc cgccacccct tccccttcc cttgatggcc tatccatttc agagcccatt aggtgctccc tccggctcct tctctggaaa agacagagcc tctcctgaat ccttagactt aactagggat accacgagtc tgaggaccaa gatgtcatct caccacctga gccaccaccc ttgttcacca gcacacccgc ccagcaccgc cgaagggctc tccttgtcgc tcataaagtc cgagtgcggc gatcttcaag atatgtctga aatatcacct tattcgggaa gtgcaatgca ggaaggattg tcacccaatc acttgaaaaa agcaaagctc atgttttttt atacccgtta tcccagctcc aatatgctga agacctactt ctccgacgta aagttcaaca gatgcattac ctctcagctc atcaagtggt ttagcaattt ccgtgagttt tactacattc agatggagaa gtacgcacgt caagccatca acgatggggt caccagtact gaagagctgt ctataaccag agactgtgag ctgtacaggg ctctgaacat gcactacaat aaagcaaatg actttgaggt tccagagaga ttcctggaag ttgctcagat cacattacgg gagttttca atgccattat cgcaggcaaa gatgttgatc cttcctggaa gaaggccata tacaaggtca tctgcaagct ggatagtgaa gtccctgaga ttttcaaatc cccgaactgc ctacaagagc tgcttcatga g
```

A nucleic acid encoding PROX1 can include a sequence having at least 80%, 85%, 90%, 95%, 99%, or 100% sequence identity to SEQ ID NO:5 or a functional fragment or variant of SEQ ID NO:5. A number of naturally occurring variants of nucleic acids encoding PROX1 and their activities are known in the art.

vi. CEBPA

CEBPA encodes a basic leucine zipper (bZIP) transcription factor which can bind as a homodimer to certain promoters and enhancers.

In one embodiment, CEBPA is represented by SEQ ID NO:6.

```
                                        (SEQ ID NO: 6)
atggagtcgg ccgacttcta cgaggcggag ccgcggcccc cgatgagcag ccacctgcag agccccccgc acgcgcccag cagcgccgcc ttcggctttc ccggggcgc gggccccgcg cagcctcccg ccccacctgc cgccccggag ccgctgggcg gcatctgcga gcacgagacg tccatcgaca tcagcgccta catcgacccg gccgccttca acgacgagtt cctggccgac ctgttccagc acagccggca gcaggagaag gccaaggcgg ccgtgggccc cacgggcggc ggcggcggcg gcgactttga ctacccgggc gcgcccgcgg gcccggcgg cgccgtcatg
```

```
cccgggggag cgcacgggcc cccgcccggc tacggctgcg cggccgccgg ctacctggac ggcaggctgg agcccctgta cgagcgcgtc ggggcgccgg cgctgcggcc gctggtgatc aagcaggagc cccgcgagga ggatgaagcc aagcagctgg cgctggccgg cctcttccct taccagccgc cgccgccgcc gccgcccctcg caccccgcacc cgcacccgcc gccgcgcac ctggccgccc cgcacctgca gttccagatc gcgcactgcg gccagaccac catgcacctg cagcccggtc accccacgcc gccgcccacg cccgtgccca gcccgcaccc cgcgcccgcg ctcggtgccg ccggcctgcc gggccctggc agcgcgctca aggggctggg cgccgcgcac cccgacctcc gcgcgagtgg cggcagcggc gcgggcaagg ccaagaagtc ggtggacaag aacagcaacg agtaccgggt gcggcgcgag cgcaacaaca tcgcggtgcg caagagccgc gacaaggcca agcagcgcaa cgtggagacg cagcagaagg tgctggagct gaccagtgac aatgaccgcc tgcgcaagcg ggtggaacag ctgagccgcg aactggacac gctgcgggc atcttccgcc agctgccaga gagctccttg gtcaaggcca tgggcaactg cgcg
```

A nucleic acid encoding CEBPA can include a sequence having at least 80%, 85%, 90%, 95%, 99%, or 100% sequence identity to SEQ ID NO:6 or a functional fragment or variant of SEQ ID NO:6. A number of naturally occurring variants of nucleic acids encoding CEBPA and their activities are known in the art.

vii. MYC

Myc (c-Myc) is a regulator gene that codes for a transcription factor, which is multifunctional, nuclear phosphoprotein that plays a role in cell cycle progression, apoptosis and cellular transformation.

In one embodiment, MYC is represented by SEQ ID NO:7.

```
                                        (SEQ ID NO: 7)
ctggattttt ttcgggtagt ggaaaaccag cagcctcccg cgacgatgcc cctcaacgtt agcttcacca acaggaacta tgacctcgac tacgactcgg tgcagccgta tttctactgc gacgaggagg agaacttcta ccagcagcag cagcagagcg agctgcagcc cccgcgcgcc agcgaggata tctggaagaa attcgagctg ctgcccaccc cgcccctgtc ccctagccgc cgctccgggc tctgctcgcc ctcctacgtt gcggtcacac ccttctccct tcggggagac aacgacggcg gtggcgggag cttctccacg gccgaccagc tggagatggt gaccgagctg ctgggaggag acatggtgaa ccagagtttc atctgcgacc cggacgacga gaccttcatc aaaaacatca tcatccagga ctgtatgtgg agcggcttct cggccgccgc caagctcgtc
```

```
                         -continued
tcagagaagc tggcctccta ccaggctgcg cgcaaagaca gcggcagccc gaacccgcc cgcggccaca gcgtctgctc cacctccagc ttgtacctgc aggatctgag cgccgccgcc tcagagtgca tcgaccctc ggtggtcttc ccctaccctc tcaacgacag cagctcgccc aagtcctgcg cctcgcaaga ctccagcgcc ttctctccgt cctcggattc tctgctctcc tcgacggagt cctccccgca gggcagcccc gagcccctgg tgctccatga ggagacaccg cccaccacca gcagcgactc tgaggaggaa caagaagatg aggaagaaat cgatgttgtt tctgtggaaa agaggcaggc tcctggcaaa aggtcagagt ctggatcacc ttctgctgga ggccacagca aacctcctca cagcccactg gtcctcaaga ggtgccacgt ctccacacat cagcacaact acgcagcgcc tccctccact cggaaggact atcctgctgc caagagggtc aagttggaca gtgtcagagt cctgagacag atcagcaaca accgaaaatg caccagcccc aggtcctcgg acaccgagga gaatgtcaag aggcgaacac acaacgtctt ggagcgccag aggaggaacg agctaaaacg gagcttttt gccctgcgtg accagatccc ggagttggaa aacaatgaaa aggccccaa ggtagttatc cttaaaaaag ccacagcata catcctgtcc gtccaagcag aggagcaaaa gctcatttct gaagaggact t ttgcggaa acgacgagaa cagttgaaac acaaacttga acagctacgg aactcttgtg cg
```

2. Vectors Encoding Hepatocyte Inducing Factors

The Hepatocyte inducing factors are introduced into a host cell using suitable transformation vectors. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, lentiviruses and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

B. Cells to be Induced

Cells that can be reprogrammed include embryonic stem cells (ESC), induced pluripotent stem cells (iPSC), fibroblast cells, adipose-derived stem cells (ADSC), neural derived stem cells, blood keratinocytes, intestinal epithelial cells and other non-hepatocyte somatic cells. In a preferred embodiment, the non-hepatocyte cell is a fibroblast cell, for example an embryonic fibroblasts (HEFs) or foreskin fibroblasts. The cells are preferably obtained from a mammal, for example, rat, mice, monkeys, dogs, cats, cows, rabbits, horses, pigs Preferably, the cells are obtained from a human subject.

C. Induced Hepatocyte Cells iHeps are disclosed, which are obtained for example, by a method which includes treating non-hepatocyte cells to overexpress the hepatic fate conversion factors HNF1A, HNF4A, and HNF6 along with the maturation factors ATF5, PROX1, and CEBPA. The non-hepatocyte is treated to overexpress at least one hepatocyte inducing factor selected from the group consisting of HNF1A, HNF4A, HNF6, ATF5, PROX1, and CEBPA. In some embodiments the non-hepatocyte is treated to overexpress or transformed to express at least 2, at least 3, at least 4 or at least 5 of the hepatocyte inducing factors. In a preferred embodiment, the cell is transformed to overexpress all 6 Hepatocyte inducing factors.

iHeps show typical and functional characteristics of hepatocytes in the organisms from which the cell induced was obtained. For example, iHeps show the typical morphology for primary human hepatocytes. iHeps express at least one hepatic marker selected from the group consisting of albumin, Cytochrome P450 (Cyp)3A4 and CypB6. Like primary human hepatocytes, hiHeps express an additional spectrum of phase I and II drug-metabolizing enzymes and phase III drug transporters and albumin. The metabolic activities of at least one of CYP3A4, CYPB6, CYP1A2, CYP2C9, and CYP2C19 are comparable between hiHeps and freshly isolated primary human hepatocytes. Preferably, the iHeps are functional as determined by the metabolic activity of these enzymes being at least 50% higher than the activity of the same enzyme in ES-Heps obtained from the same organism. The activity of the enzyme can be 55%, 60%, 65%, 70%, 75%, 80%, 85%, 90%, 95%, 100% or more, higher than the activity in ES-Heps. Most preferably, the activities of all these CYP enzymes in hiHeps are at least 100-fold higher than that of ES-Heps.

In some embodiments, MYC expression levels in iHeps are lower than the levels found in normal hepatocytes in the corresponding organism as measured for example, by quantitative reverse transcriptase polymerase chain reaction (RTqPCR), i.e., if the donor organism for the non-hepatocyte cell to be induced is a human subject, the levels are compared to normal hepatocytes found in humans.

Functional hiHeps may also express at least one drug metabolic phase II enzyme or phase II transporter selected from the group consisting of UDP glucuronosyltransferase (UGT)1A1, UGT1A3, UGT1A4, UGT1A6, UGT1A9, GSTA1, UGT2B7, UGT2515, Microsomal glutathione-S-transferase 1 (MGST1), nicotinamide N-methyltransferase (NNMT), NTCP, organic anion-transporting polypeptide 1B3 (OATP1B3), Multidrug resistance protein(MRP)6, MRP2, Flavin-containing monooxygenase 5 (FMO5), Monoamine oxidase (MAO)A, MAOB, and epoxide hydrolase 1 (EPHX1). Preferably, endogenous expression of Forkhead box (FOX)A1, FOXA2, FOXA3 and Liver receptor homolog 1 (LRH1) is activated in hiHeps.

In some embodiment where the cell being induced is not an epithelial cell, hiHeps additionally express at least one epithelial cell marker, for example, E-cadherin, and where the cell being induced is a fibroblast, the hiHeps obtained following induction of fibroblasts using the methods disclosed herein, do not express the fibroblast marker genes such as COLIA1, PDGFRB, THY1 and α-fetoprotein as measured for example by RT-PCR.

With respect to functional characteristics associated with mature hepatocytes, hiHeps possess at least one characteristic selected from the group consisting of: albumin secretion, LDL uptake, indocyanine green (ICG) incorporation from cell culture medium and exclusion of the absorbed ICG after withdrawal, glycogen synthesis and storage, and fatty droplet accumulation.

III. Method of Making

Huang, et al., *Nature,* 475:386-389 (2011) disclose the direct induction of hepatocyte-like cells from mouse tail-tip fibroblasts by transduction of Gata4, Hnf1α and Foxa3, and inactivation of p19(Arf). Induced cells show typical epithelial morphology. Sekiya and Suzuki, *Nature,* 475:390-393 (2011)), identified three specific combinations of two transcription factors, Hnf4α plus Foxa1, Foxa2 or Foxa3, that can convert mouse embryonic and adult fibroblasts into cells that resemble hepatocytes in vitro. Cai, et al., *Hepatology,* 45(5):1229-39 (2007) disclose a three-stage method to direct the differentiation of human embryonic stem cells (hESCs) into hepatic cells in serum-free medium. Human ESCs were first differentiated into definitive endoderm cells by 3 days of Activin A treatment. Next, the presence of fibroblast growth factor-4 and bone morphogenetic protein-2 in the culture medium for 5 days induced efficient hepatic differentiation from definitive endoderm cells, followed by 10 days of further in vitro maturation. Zhao, et al., *Cell Res.,* 23(1):157-161 (2013) disclose a method of promoting the maturation of hESCs into cells with hepatocyte-like properties by inducing expression of PROX1 and HNF6.

In the methods disclosed herein, the non-hepatocyte is reprogrammed into an iHep by upregulating Hepatocyte inducing factors in the cell, optionally in combination with upregulating MYC and downregulating p53 and culturing the cells for a sufficient period of time as disclosed herein to convert the cell into a cell with hepatocyte-like properties. The non-hepatocyte cells to be induced are obtained from the donor animal using methods known in the art. The cells are placed in culture and cultured using methods that are known in the art.

Figure 1B:
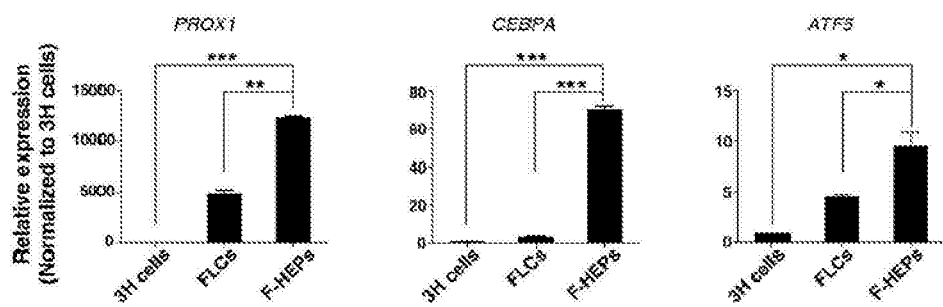
FIG. 1B is a bar graph showing a quantitative comparison of the expression of hepatic transcription factors in 3H cells, fetal liver cells (FLCs), and F-HEPs. n=2. *p<0.05; p<0.01; *p<0.001.
Figure 1C:
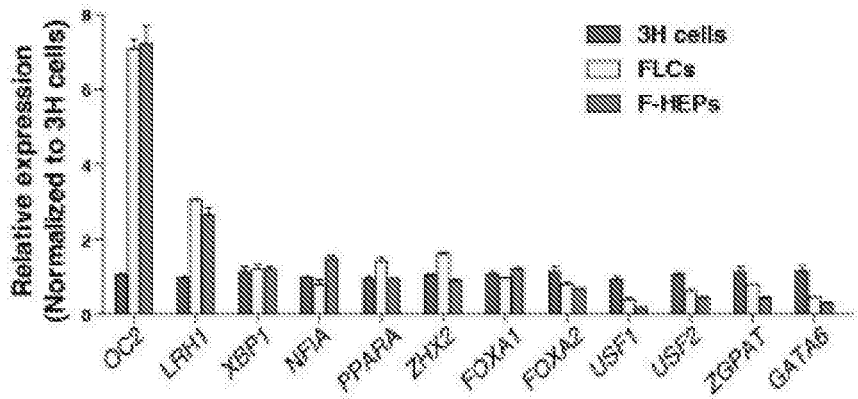
FIG. 1C is a bar graph showing gene expression analysis of liver-enriched transcription factors in 3H cells, FLCs and F-HEPs by qRT-PCR. n=2.
Figure 1D:
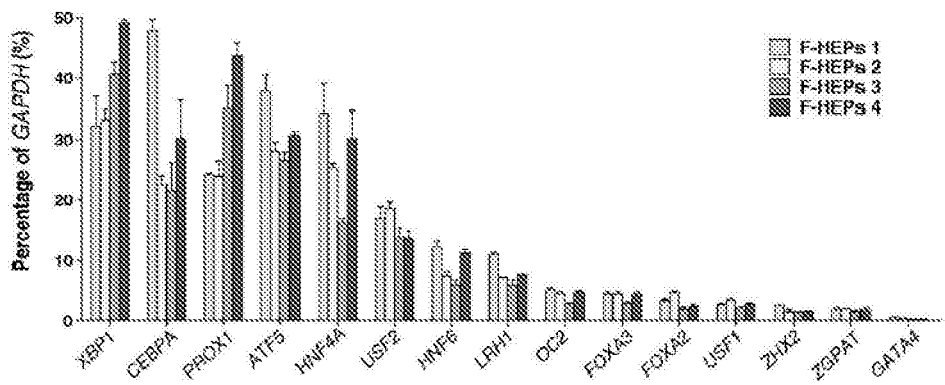
FIG. 1D is a bar graph showing a quantitative analysis of the abundance of hepatic transcription factors in four individual F-HEPs. n=2.
Figure 1E:
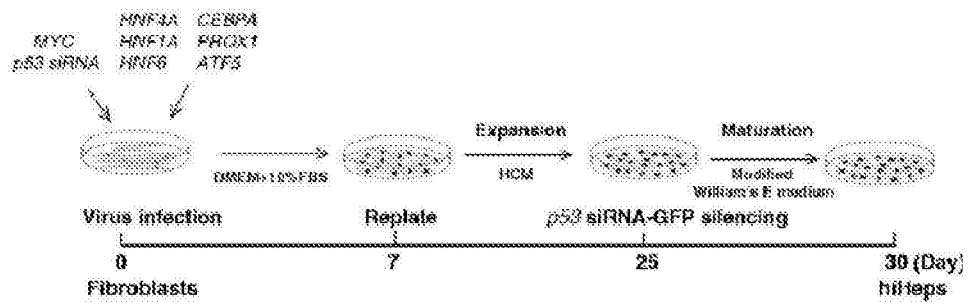
FIG. 1E is a schematic view of the hiHep reprogramming diagram.

The reprogramming method includes the following steps: (a) treat the cells to upregulate hepatocyte inducing factors and culture the cells in cell culture medium (transformation phase); (b) replate and culture the cells in HCM (expansion phase), and (c) a maturation phase, where cells are cultured in a hepatocyte maturation medium. A schematic for the disclosed method is shown in FIG. 1E. At the transformation phase, the cells are treated to upregulate at least one hepatocyte inducing factor selected from the group consisting of HNF1A, HNF4A, HNF6, ATF5, PROX1, and CEBPA. Preferably, the cells are additionally treated to upregulate MYC and/or downregulate p53.

In the transformation phase, the treated cells are cultured for a sufficient length of time in conventional cell culture medium, for example, Dulbecco's Modified Eagle's medium (DMEM). Preferably, the cells are cultured for at least 7 days in this first step, to about 80% confluence. The cells then replated and expanded in HCM for a period of about 15 to 30 days, preferably for about 18-30 days, and more preferably, for about 18 days (expansion phase), and then transferred to modified William's E medium for a period of about 5 days (maturation phase), following which induced hepatocytes are harvested. Preferably, p53 siRNA is downregulated at the end of the expansion phase, for example at about day 20-30 post infection, preferably, at about day 25 post infection, before the cells are transferred into the modified William's E medium (FIG. 1E). We observe silence of p53 siRNA around 25 days post infection. The silence is mainly caused by the introduction of hepatic transcription factors. For example, HNF4A and CEBPA can substantially decrease proliferative rate of iHeps. Furthermore, the self-establishment of endogenous hepatic maturation signaling network also attenuate the reliability of exogenous expression of other transcription factors (FIG. 2).

The method includes a step confirming that the non-hepatocytes have acquired hepatocyte-like properties, using morphological and functional characteristics as well as gene expression.

Morphological confirmation methods include the confirmation of morphological characteristics specific for hepatocytes such as cells having a plurality of nuclei observed by a phase microscope and granules rich in cytoplasm observed by an electron microscope, in particular, the presence of glycogen granules.

Treated cells can also be identified as induced hepatocytes using one or more of the following characteristics: their ability to express ALB at a level comparable to that of primary human hepatocytes; expression of one or more of the five major cytochrome P450 enzymes, CYP3A4, CYP1A2, CYP2C9, and CYP2C19; expression of phase II enzyme or phase II transporter selected from the group consisting of UGT1A1, UGT1A3, UGT1A4, UGT1A6, UGT1A9, GSTA1, UGT2B7, UGT2515, MGST1, NNMT, NTCP, OATP1B3, MRP6, MRP2, FMO5, MAOA, MAOB, and EPHX1. Successful induction can be confirmed by the presence of an epithelial marker and the absence of a marker for the cell which is being induced. For example, where the cell being induced is a fibroblast, additional indication that the cells has been induced into a hepatocyte-like cell can be expression of at least one epithelial cell marker, for example, E-cadherin, and absence of expression of the fibroblast marker genes such as COLIA1, PDGFRB, THY1 and α-fetoprotein as measured for example by RT-PCR.

A. Upregulating Hepatocyte Inducing Factors and MYC

Hepatocyte inducing factors and MYC are upregulated by contacting the non-hepatocyte with factors which upregulate gene expression and or protein levels/activity of the Hepatocyte inducing Factors and MYC. These factors include, but are not limited to nucleic acids, proteins and small molecules.

For example, upregulation may be accomplished by exogenously introducing the nucleic acids encoding the hepatocyte inducing Factor(s) and optionally, MYC, into the non-hepatocyte (host cell). The nucleic acid may be homologous or heterologous. The nucleic acid molecule can be DNA or RNA, preferably, mRNA. Preferably, the nucleic acid molecule is introduced into the non-hepatocyte cell by lentiviral expression.

The host cell is transformed to overexpress at least one hepatocyte inducing factor selected from the group consisting of HNF1A, HNF4A, HNF6, ATF5, PROX1, and CEBPA. Preferably, the cell is additionally transformed overexpress the proliferation factor MYC. In some embodiments the cell is transformed to express at least 2, at least 3, at least 4 or at least 5 of the hepatocyte inducing factors. In a preferred embodiment, the cell is transformed to overexpress all 6 Hepatocyte inducing factors.

Vectors containing nucleic acids to be expressed can be transferred into host cells. Nucleic acids can be transfected into mammalian cells by techniques including, for example, calcium phosphate co-precipitation, DEAE-dextran-mediated transfection, lipofection, electroporation, or microinjection. The Ex vivo methods disclosed herein can include, for example, the steps of harvesting cells from a subject/donor, culturing the cells, transducing them with an expression vector, and maintaining the cells under conditions suitable for expression of the encoded polypeptides. These methods are known in the art of molecular biology.

Upregulation may also be accomplished by treating the cells with factors known to increase expression of genes encoding the Hepatocyte inducing factors/MYC and/or factors known to increase the corresponding protein levels. For example, Zhao, et al., *Cell Res.,* 23(1):157-161 (2013), disclose a method for promoting the emergence of PROX1 and HNF6-expressing cells from hESCs using the induction factors FGF7, BMP2 and BMP4. Known factors, including small molecules and/or proteins which upregulate Hepatocyte inducing factors gene expression or protein levels can also be use.

B. Downregulating p53 p53 can be downregulated by treating cells to downregulate p53 gene expression, mRNA levels or protein levels. This step includes contacting the cells with any molecule that is known to downregulate p53 gene expression, mRNA or protein levels, including but not limited to nucleic acid molecules, small molecules and protein.

p53 gene expression can be inhibited using a functional nucleic acid, or vector encoding the same, selected from the group consisting of antisense oligonucleotides, siRNA, shRNA, miRNA, EGSs, ribozymes, and aptamers. Preferably, p53 gene expression is inhibited using siRNA, shRNA, or miRNA.

1. RNA Interference

In some embodiments, P53 gene expression is inhibited through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) *Cell,* 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

2. Antisense p53 gene expression can be inhibited by antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the p53 encoding mRNA. Antisense nucleic acid sequences and delivery methods are well known in the art (Goodchild, *Curr. Opin. Mol. Ther.*, 6(2):120-128 (2004); Clawson, et al., *Gene Ther.*, 11(17):1331-1341 (2004)). The antisense nucleic acid can be complementary to an entire coding strand of a target sequence, or to only a portion thereof. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire p53 mRNA sequence, but can also be an oligonucleotide that is antisense to only a portion of the p53 mRNA. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Other examples of useful antisense oligonucleotides include an alpha-anomeric nucleic acid. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.*, 215:327-330 (1987)).

3. Aptamers

In some embodiments, the inhibitory molecule is an Aptamer. Aptamers are molecules that interact with a target molecule, preferably in a specific way. Aptamers can bind the target molecule with a very high degree of specificity. For example, aptamers have been isolated that have greater than a 10,000 fold difference in binding affinities between the target molecule and another molecule that differ at only a single position on the molecule. Because of their tight binding properties, and because the surface features of aptamer targets frequently correspond to functionally relevant parts of the protein target, aptamers can be potent biological antagonists. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

4. Ribozymes p53 gene expression can be inhibited using ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

5. Triplex Forming Oligonucleotides p53 gene expression can be inhibited using triplex forming molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

6. External Guide Sequences p53 expression can be inhibited using external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

7. ShRNA p53 expression can be inhibited using small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., *Nature Biotechnol.* 20:500-505 (2002); Miyagishi and Taira, *Nature Biotechnol.* 20:497-500 (2002); Paddison et al., *Genes Dev.* 16:948-958 (2002); Paul et al., *Nature Biotech-* nol. 20:505-508 (2002); Sui (2002) supra; Yu et al., *Proc. Natl. Acad. Sci. USA* 99(9):6047-6052 (2002).

C. Delivery Vehicles

Methods of making and using vectors for in vivo expression of functional nucleic acids such as antisense oligonucleotides, siRNA, shRNA, miRNA, EGSs, ribozymes, and aptamers are known in the art.

For example, the delivery vehicle can be a viral vector, for example a commercially available preparation, such as an adenovirus vector (Quantum Biotechnologies, Inc. (Laval, Quebec, Canada). The viral vector delivery can be via a viral system, such as a retroviral vector system which can package a recombinant retroviral genome. The recombinant retrovirus can then be used to infect and thereby deliver to the infected cells nucleic acid encoding the hepatocyte inducing factor(s). The exact method of introducing the altered nucleic acid into the host cell is, of course, not limited to the use of retroviral vectors. Other techniques are widely available for this procedure including the use of adenoviral vectors, adeno-associated viral (AAV) vectors, lentiviral vectors, pseudotyped retroviral vectors, and others described in (Soofiyani, et al., *Advanced Pharmaceutical Bulletin*, 3(2):249-255 (2013). Viruses can be modified to enhance safety, increase specific uptake, and improve efficiency (see, for example, Zhang, et al., *Chinese J Cancer Res.*, 30(3):182-8 (2011), Miller, et al., *FASEB J*, 9(2):190-9 (1995), Verma, et al., *Annu Rev Biochem.*, 74:711-38 (2005)).

Physical transduction techniques can also be used, such as liposome delivery and receptor-mediated and other endocytosis mechanisms (see, for example, Schwartzenberger et al., *Blood*, 87:472-478 (1996)). Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. In addition, nucleic acid or vectors encoding the hepatocyte inducing factors can be delivered in vivo by electroporation as well as by means of a sonoporation. During electroporation electric pulses are applied across the cell membrane to create a transmembrane potential difference, allowing transient membrane permeation and transfection of nucleic acids through the destabilized membrane (Soofiyani, et al., *Advanced Pharmaceutical Bulletin*, 3(2):249-255 (2013)). Sonoporation combines the local application of ultrasound waves and the intravascular or intratissue administration of gas microbubbles to transiently increase the permeability of vessels and tissues (Escoffre, et al., *Curr Gene Ther.*, 13(1):2-14 (2013)). Electroporation and ultrasound based techniques are targeted transfection methods because the electric pulse or ultrasound waves can be focused on a target tissue or organ and hence gene delivery and expression should be limited to thereto. Expression or overexpression of the disclosed hepatocyte inducing factors accomplished with any of these or other commonly used gene transfer methods, including, but not limited to hydrodynamic injection, use of a gene gun.

IV. Method of Using

The studies disclosed herein show that human hepatocytes with drug metabolic function can be generated by lineage reprogramming, thus providing a cell resource for pharmaceutical applications.

A. In Vitro and Research Applications (1) Drug Testing

Liver parenchymal cells play a key role in drug development because the liver plays a central role in the metabolic activity of the drug. At present, the main cause of failure of a drug candidate is its ADME (absorption, distribution, metabolism, excretion) is not ideal. An essential part of drug discovery research is to the metabolic and toxicological effects of the candidate drug on liver cells, human liver parenchymal cells with full participation of drug metabolism. Currently the main hepatocytes used for in vitro drug development are human adult primary hepatocytes. Due to their limited sources, and the difficulty of maintaining primary hepatocyte function in vitro is difficult to maintain, their application in drug development is quite limited, hiHeps disclosed herein which express phase I, II and III drug-metabolizing enzymes can be used in vitro drug metabolism studies.

(ii) Research

The problem encountered in studies involving infectious diseases is the lack of adequate animal models. hiHeps can be used to construct humanized mouse models for study of infectious diseases, for example, hepatitis B and C infections. These animal models can provide a reliable in vivo platform for use in the development of vaccines and drugs for treating infectious diseases, particularly diseases that infect the liver.

B. In Vivo Applications

Liver failure and loss of function is one of the most severe consequences of liver disease. Because of its rapid onset, rapid progression, liver transplantation is the primary means of treatment of these diseases. However, donor scarcity presents a serious problem and many patients die while waiting for liver transplantation.

The studies disclosed herein show that transplanted hiHeps repopulate up to 30% of the livers of Tet-uPA/Rag2$^{-/-}$γc$^{-/-}$ mice and secrete more than 300 mg/ml human albumin in vivo. Thus, hiHeps can be used in the treatment of liver failure and loss of function diseases, for example.

Transplanting isolated iHeps by percutaneous or transjugular infusion into the portal vein, or injecting into the splenic pulp or the peritoneal cavity, is a less invasive procedure compared with liver transplantation. The iHeps are preferably obtained from the same animal being treated. As the host liver is not removed or resected, the loss of graft function should not worsen liver function. Furthermore, isolated iHeps could be, potentially, cryopreserved for ready access. The iHeps can be used as a vehicle for ex vivo gene therapy for example, for rescuing patients from radiation-induced liver damage resulting from radiotherapy for liver tumors. iHeps can be transplanted into a recipient organism using a carrier such as a matrix known for transplantation of hepatocytes. For example, Zhou, et al., *Liver Transpl.*, 17(4):418-27 (2011) discloses the use of decellularized liver matrix (DLM) as a carrier for hepatocyte transplantation. Schwartz, et al., Int. J. Gastroentrol., 10(1): discloses isolating liver and pancreas cells from tissue samples, seeding onto a poly-L-lactic acid matrix and re-implanting into the mesentery of the same patient.

hiHeps can also be used in the bio-artificial liver support systems. Bioartificial liver support system based on the disclosed cells are constructed to temporarily replace the main function of liver failure (remove hazardous substances, provide the liver synthetic biologically active substances), to stabilize and improve the patient's internal environment, until a suitable donor source for transplantation is available.

Methods for making bioartifical liver are disclosed for example in U.S. Publication No. 2008/0206733.

V. Kits

Kits for inducing in vitro reprogramming of non-hepatocytes into induced heptocytes with functional hepatocyte metabolic properties are disclosed. The kit includes factors which up-regulate hepatocyte inducing factors HNF1A, HNF6, HNF4A, ATF5, PROX1, CEPBA, and/or MYC and factors which downregulate p53 gene expression and/or protein activity. In one embodiment, the kit includes any DNA sequence of HNF1A, HNF6, HNF4A, ATF5, PROX1, CEPBA, and/or MYC and DNA sequence to downregulate p53 gene expression. In a preferred embodiment, the kit includes lentiviruses which overexpress HNF1A, HNF6, HNF4A, ATF5, PROX1, CEPBA, and/or MYC gene and nucleic acid which inhibits p53 gene expression.

Examples

Materials and Methods
Human Primary Cell Isolation and Culture

The present study was approved by the Clinical Research Ethics Committee of China-Japan Friendship Hospital (Ethical approval No: 2009-50), Stem Cell Research Oversight of Peking University (SCRO201103-03) and conducted according to the principles of the Declaration of Helsinki.

Human embryonic skins and fetal liver tissues at 14 gestational weeks were obtained from abortion with informed patient consent. Fetal liver cells were obtained as previously described (Lilja et al., 64:1240-1248 (1997)). The fetal liver tissue was cut into 1-3 mm³ fragments for digestion in 10 ml medium (RPMI 1640) supplemented with 1 mg/ml collagenase IV (Gibco). Digestion was performed at 37° C. for 15-20 min and erythrocytes were eliminated by slow-speed centrifugation. Cells were washed with RPMI 1640 medium for 3 times. Trypan blue exclusion estimated that cell viability was 90%.

Fresh human embryonic skin tissue (HEF) and ex vivo human adult foreskin tissue (HFF) were sterilized with 75% aqueous ethanol and washed with phosphate buffered saline (PBS). The tissue was carefully separated from subcutaneous tissue with ophthalmic scissors. The tissue was washed several times with PBS, small tissue blocks were seeded in a petri dish, and placed in an incubator at 37° C., 5% CO2. Two hours later, the following were added: DMEM high glucose medium (purchased from Hyclone company, product catalog No. SH30022.01B), 15% fetal bovine serum (FBS), 0.1 mM β-mercaptoethanol, 1% non-essential amino acids, and 1 mM Glutamate, 8 units/ml gentamicin). Cells were digested with 0.25% trypsin and 0.02% EDTA at room temperature for 5 minutes. Cells were seeded at 1:3 in the above-described DMEM high glucose medium in a new Petri dish. Medium was changed every two days, and cells were passaged 1:3 every 4 days to obtain human fibroblasts (derived from fetal skin) and human fibroblasts (derived from adult foreskin). Human skin fibroblasts get to about 80% confluence following cell culture for about 5-7 days.

Human primary hepatocytes were isolated from human donor livers not used for liver transplantation, following informed consent (Seglen, 13:29-83 (1976)) and cultured with HCM (LONZA).

Generation of hiHeps

This study was approved by the Clinical Research Ethics Committee of the China-Japan Friendship Hospital (ethical approval 2009-50) and Stem Cell Research Oversight of Peking University (SCRO201103-03), and conducted according to the principles of the Declaration of Helsinki.

Human fibroblasts were infected overnight and cultured in DMEM plus 10% fetal bovine serum for 1 week before transfer into hepatocyte culture medium (HCM) (Lonza) for expansion.

One day before viral infection, human fibroblasts were seeded at 20,000 cells/well into 12-well cell culture plates containing mammalian somatic cell culture medium, and cultured at 37° C. and 5% carbon dioxide culture for 12 hours; then thereto was added the following lentivirus expression vectors: lentivirus expression vectors expressing HNF1A, HNF6, HNF4A, ATF5, PROX1, CEBPA and MYC, respectively and a lentivirus expressing a DNA(s) for inhibiting the expression of p53, 10 µl for HNF1A, 10 µl for HNF6, 6 µl for HNF4A, 10 µl for ATF5, 3 µl for PROX1, 3 µl for CEBPA, 10 µl for MYC and 10 µl for p53 (lentivirus for inhibiting the expression of p53). The medium was changed after 20 hours, after which the medium was changed every day. Cells were cultured for 7 days in DMEM and then transferred into HCM.

After 3 weeks of culture, HCM was replaced by modified William's E medium (Beijing Vitalstar Biotechnology). Cells were passaged every 4 days, and human hepatocyte-like cells were harvested after 30 days. A schematic for hiHep reprogramming is shown in FIG. 1E.

Growth Curve and Doubling Times

For MTT assays, the induced cells of expansion stage and maturation stage were plated into 96-well plate (1000 cells per well) and cultured in HCM (before p53 siRNA-GFP silence) or modified WEM (after p53 siRNA-GFP silence) separately for 7 days. MTT assay was done at each day according to the manufacturer's instructions (Vybrant® MTT Cell Proliferation Assay Kit, Invitrogen). To calculate the doubling time of the induced cells in the expansion stage, the induced cells in the expansion stage (before p53 siRNA-GFP silence) were plated at the density of 30000 cells per well, and cultured in 12-well plate coated with matrigel. The growth rate was determined by counting the number of cells using a hemacytometer as a function of time. Data from the exponential phase of growth (data points at 12, 24, 36 and 48 h) were used to obtain an exponential growth curve. Doubling time (Td) was then obtained using the formula: Td=t*ln 2/ln(Nt/N0) where Nt is the cell number at time t; N0 is the cell number at the initial time.

Hepatic Differentiation

Human embryonic stem cells (hESCs, ES cell line H1, WiCell research institute) were maintained on irradiated mouse embryonic fibroblasts in hESCs medium (Thomson et al., *Science* 282:1145-1147 (1998)). hESCs were differentiated into hepatocytes as previously reported (Zhao et al., *Cell Res* 23:157-161 (2013)).

Molecular Cloning, Lentivirus Production and Transduction

Complementary DNAs of transcriptional factors are amplified from the human full-length TrueClones™ (Origene) and inserted into pCDH-EF1-MCS-T2A-Puro (System Biosciences) according to user's manual (for each of lentivirus expression vectors of HNF1A, HNF6, HNF4A, ATF5, PROX1, and CEBPA, SEQ ID NOs: 1-6 are inserted into restriction enzyme sites of pCDH-EF1-MCS-T2A-Puro, respectively). Lentivirus expression vector of MYC is constructed by inserting SEQ ID NO:7 into restriction enzyme sites (Xho I and EcoR I) of expression vector pLL-IRES-Puro (Zhao Y et al., Cell Stem Cell. 2008 Nov. 6; 3(5): 475-9; available from Beijing Vitalstar Biotechnology, Ltd. or Peking University. For full sequence information, see http://www.sciencegateway.org/protocols/lentivirus/pllmap.html). Lentivirus for inhibiting the expression of p53 is constructed as follows: DNA molecule for interfering with the expression of p53 is inserted into restriction enzyme sites (Hpa I and Xho I) of expression vector pll3.7 (Rubinson and Dillon et al., Nature Genetics, 2003; available from Beijing Vitalstar Biotechnology, Ltd. or Peking University). The DNA molecule for interfering with the expression of p53 is obtained by annealing with a sense chain (5'-TGACTCCAGTGGTAATCTACTTCAAGAGAGTAGAT-TACCACTGGA GTCTTTTTTC-3') and a antisense chain (5'-TC GAGAAAAAAGACTCCAGTGGTAATC-TACTCTCTTG AAGTAGATTACCACTGGAGT CA-3'). Virus package is conducted as described previously (Zhao et al., *Cell Stem Cell,* 3:475-479 (2008)). Human fibroblasts are infected in DMEM (Hyclone) with 10% fetal bovine serum, containing 10 μg/ml polybrene for 12 hours. The fibroblasts were replated seven days post infection and cultured in HCM (LONZA). At about 25 days post infection when p53 siRNA was silenced as indicated by a GFP reporter, hiHeps were cultured in modified William's E Medium (Vitalstar Biotechnology).

Albumin ELISA, Periodic Acid-Schiff (PAS) Staining, Indocyanine Green (ICG) Uptake and Release, Low-Density Lipoprotein (LDL) Uptake and Oil Red Staining Human Albumin was measured using the Human Albumin ELISA Quantitation kit (Bethyl Laboratory). The PAS staining system was purchased from Sigma-Aldrich. Cultures were fixed with 4% paraformaldehyde (DingGuo) and stained according to the manufacturer's instructions. ICG uptake and release was performed as previously described (Cai et al., *Hepatology* 45:1229-1239 (2007)). For LDL uptake assay, 10 μg/ml DiI-Ac-LDL (Invitrogen) was incubated with hiHeps for 4 h at 37° C. and observed by fluorescence microscopy. For lipid detection, cultures were fixed with 4% paraformaldehyde and treated with 60% isopropanol for 5 min. Then the isopropanol was removed and Oil Red O working solution was added and incubated for 15 min at room temperature. Then the Oil Red O was removed and cultures rinsed with until clear.

CYP Metabolism Assay

Drug metabolic activity was evaluated using the traditional suspension method as previously described (Gebhardt et al., Drug Metab. Rev. 35:145-213 (2003)). hiHeps were cultured in the medium with 50 mM rifampicin, 50 mMb-naphthoflavone, and 1 m Mphenobarbital for 72 hr and refreshed every 24 hr. Cell viability of dissociated hiHeps, HepG2 cells, ES-Heps, fibroblasts, and freshly isolated primary human hepatocytes was measured by trypan blue. One milliliter of prewarmed incubation medium (William's E medium, 10 mM HEPES [pH 7.4], 2 mM GlutaMAX) was added per 1 3 106 total cells (cell suspension). The substrate solutions were prepared with the same incubation medium [400 mM testosterone, 10 mM midazolam, 200 mM phenacetin, 1 mM bupropion, 500 mM (S)-mephenytoin, 50 mM diclofenac]. The reactions were started by mixing 250 ml of the substrate solution with 250 ml of cell suspension in a 5 ml polystyrene round-bottom tube (BD Falcon). The tubes were put in an orbital shaker in the incubator and the shaker speed was adjusted to 210 rpm. After a 15-240 min incubation at 37° C., the tubes were centrifuged at room temperature to collect the supernatant. The reactions were stopped by addition of sample aliquots to tubes containing triple the volume of quenching solvent (methanol) and frozen at −80° C. Isotope-labeled reference metabolites were used as internal standards. Internal reference metabolites for testosterone, midazolam, (S)-mephenytoin, diclofenac, bupropion, and phenacetin are 6b-hydroxytestosterone-[D7], hydroxymidazolam-[13C3], 40-hydroxymephenytoin-[D3], 40-hydroxydiclofenac-[13C6], hydroxybupropion-[D6], and acetomidophenol-[13C2, 15N], respectively. The metabolites were used to make standard curves for the metabolite analyses. Standard metabolites were 6b-hydroxytestosterone, 10-hydroxymidazolam, hydroxybupropion, 40-hydroxydiclofenac, (±)-40-hydroxymephenytoin, and acetaminophen. The metabolites were quantified by Pharmaron using validated traditional LC-MS methods. The results are expressed as picomoles of metabolite formed per minute and per million cells. Chemicals were purchased from Sigma including b-naphthoflavone, rifampicin, testosterone, midazolam, diclofenac, and phenacetin. Standard metabolites and internal reference metabolites were purchased from BD Biosciences. Phenobarbital was a kind gift from Jinning Lou.

qRT-PCR and RT-PCR

Total RNA was isolated by RNeasy Micro Kit (Qiagen) and then reverse-transcribed with SuperScript® III First-Strand Synthesis (Invitrogen). RT-PCR was performed with 2×EasyTaq PCR SuperMix (TransGen) following the manufacturer's instructions. Primers used for specific detection of endogenous gene expression are shown in Tables 1 and 2.

TABLE 1

Figure 2A:
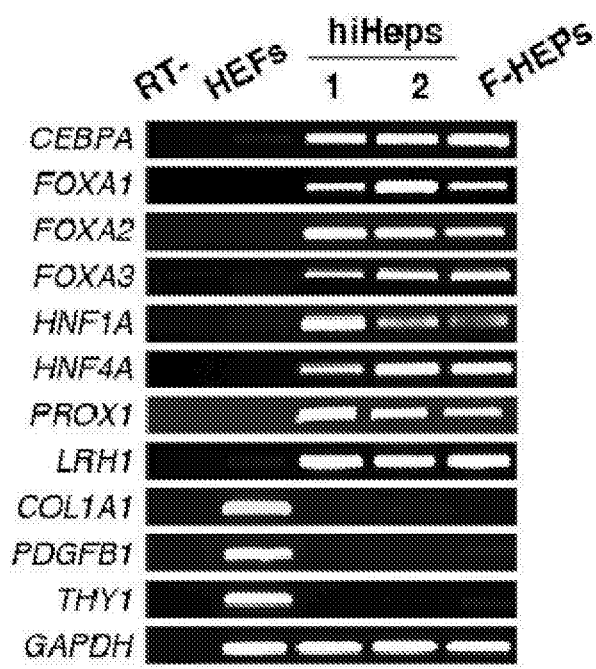
FIG. 2A shows endogenous gene expression analysis of hepatic transcription factors and fibroblast markers in hiHeps by RT-PCR.

Primers used for specific detection of endogenous genes in FIG. 2A

| Gene | Forward Primer (5'→3') | Reverse Primer (5'→3') |
|---|---|---|
| CEBPA | AGCATTGCCTAGGAACACGAA (SEQ ID NO: 8) | CCCCAGGATCAAAAGTAATCCCA (SEQ ID NO: 9) |
| FOXA1 | TACTCCTTCAACCACCCGTTC (SEQ ID NO: 10) | GCTATGCCAGACAAACCCC (SEQ ID NO: 11) |
| FOXA2 | CCTACGAACAGGTGATGCACT (SEQ ID NO: 12) | GATTTCTTCTCCCTTGCGTCT (SEQ ID NO: 13) |
| FOXA3 | CGCCCTACAACTTCAACCAC (SEQ ID NO: 14) | GATCAGGCCCCAAGAGCTTC (SEQ ID NO: 15) |
| HNF1A | GCCTCTTCCTCCCAGTAACCA (SEQ ID NO: 16) | TATCCCACGAAGCAGCGACA (SEQ ID NO: 17) |
| HNF4A | AGAAAGAGGCAGACCATCCAC (SEQ ID NO: 18) | TCCCTGCATACTCCTTGAAGC (SEQ ID NO: 19) |

TABLE 1-continued

Primers used for specific detection of endogenous genes in FIG. 2A

| Gene | Forward Primer (5'→3') | Reverse Primer (5'→3') |
| --- | --- | --- |
| HNF6 | GCAGCTCCAATTCAGGCAAC (SEQ ID NO: 20) | CATCATTTGTCTTGCCAAGTCG (SEQ ID NO: 21) |
| LRH1 | CAGATGCCGGAAAACATGCAA (SEQ ID NO: 22) | CTTAAGTCCATTGGCTCGGAT (SEQ ID NO: 23) |
| COL1A1 | GGACACCACCCTCAAGAGCC (SEQ ID NO: 24) | GTCATGCTCTCGCCGAACCAG (SEQ ID NO: 25) |
| PDGFRB | ATTCCATGCCGAGTAACAGACCC (SEQ ID NO: 26) | AGTTGACCACCTCATTCCCGAT (SEQ ID NO: 27) |
| THY1 | GCGATTATCTACCCACGTCCAC (SEQ ID NO: 28) | ACAGACCATGTCCGTGCTA (SEQ ID NO: 29) |
| PROX1 | CCGAACTGCCTACAAGAGC (SEQ ID NO: 30) | AAGGCAGAAAGAAAACAACCA (SEQ ID NO: 31) |
| GAPDH | TCTTCCAGGAGCGAGATCCCT (SEQ ID NO: 32) | TGGTCATGAGTCCTTCCACGAT (SEQ ID NO: 33) |

TABLE 2

Figure 2B:
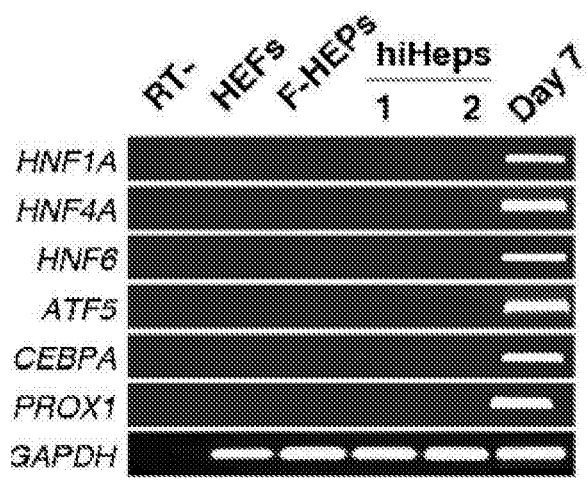
FIG. 2B shows the silence of exogenous genes detected by RT-PCR. Day 7, 7 days post infection.

Primers used for specific detection of exogenous genes in FIG. 2B

| Gene | Forward Primer (5'→3') | Reverse Primer (5'→3') |
| --- | --- | --- |
| CEBPA | TGCCTCCTGAACTGCGTCC (SEQ ID NO: 34) | GCTCCGCCTCGTAGAAGTCG (SEQ ID NO: 35) |
| HNF1A | CCGTCTAGGTAAGTTTAAAGCTC (SEQ ID NO: 36) | CTCCGGGTAGTAGCTCCAC (SEQ ID NO: 37) |
| HNF4A | CCGTCTAGGTAAGTTTAAAGCTC (SEQ ID NO: 38) | GTGTCATTGCCCATCGTCA (SEQ ID NO: 39) |
| HNF6 | CCGTCTAGGTAAGTTTAAAGCTC (SEQ ID NO: 40) | CCGATCGCTTCCATGGTCAG (SEQ ID NO: 41) |
| PROX1 | CCGTCTAGGTAAGTTTAAAGCTC (SEQ ID NO: 42) | CGTCCTTTTCACTCCAATGTCA (SEQ ID NO: 43) |
| ATF5 | CCGTCTAGGTAAGTTTAAAGCTC (SEQ ID NO: 44) | GTGAAATCAACTCGCTCAGTC (SEQ ID NO: 45) | qRT-PCR was performed using Power SYBR® Green PCR Master Mix (Applied Biosystems) on MX3000P Sequence Detection System (Stratagene). Primers used are shown in Table 3.

TABLE 3

Primers used for qRT-PCR, Related to FIG. 3

| Gene | Forward Primer (5'→3') | Reverse Primer (5'→3') |
| --- | --- | --- |
| ALB | GCACAGAATCCTTGGTGAACAG (SEQ ID NO: 46) | ATGGAAGGTGAATGTTTCAGCA (SEQ ID NO: 47) |
| CEBPA | ACAAGAACAGCAACGAGTACCG (SEQ ID NO: 48) | CATTGTCACTGGTCAGCTCCA (SEQ ID NO: 49) |
| FOXA1 | GTGGCTCCAGGATGTTAGGA (SEQ ID NO: 50) | AGGCCTGAGTTCATGTTGCT (SEQ ID NO: 51) |
| FOXA2 | CGACTGGAGCAGCTACTATGC (SEQ ID NO: 52) | TACGTGTTCATGCCGTTCAT (SEQ ID NO: 53) |

TABLE 3-continued

Primers used for qRT-PCR, Related to FIG. 3

| Gene | Forward Primer (5'→3') | Reverse Primer (5'→3') |
|---|---|---|
| FOXA3 | CTGGCCGAGTGGAGCTACTA (SEQ ID NO: 54) | AGGGGGATAGGGAGAGCTTA (SEQ ID NO: 55) |
| HNF1A | CCATCCTCAAAGAGCTGGAG (SEQ ID NO: 56) | GTGCTGCTGCAGGTAGGACT (SEQ ID NO: 57) |
| HNF4A | CCAAAACCCTCGTCGACATG (SEQ ID NO: 58) | TTCTCAAATTCCAGGGTGGTGTA (SEQ ID NO: 59) |
| HNF6 | TGTGGAAGTGGCTGCAGGA (SEQ ID NO: 60) | TGTGAAGACCAACCTGGGCT (SEQ ID NO: 61) |
| ONECUT2 | CGAACACTCTTCGCCATCTTC (SEQ ID NO: 62) | GTTGCTGACGGTTGTGAGCTC (SEQ ID NO: 63) |
| PROX1 | ACAGGGCTCTGAACATGCAC (SEQ ID NO: 64) | GGCATTGAAAAACTCCCGTA (SEQ ID NO: 65) |
| LRH1 | CGAGTGGGCCAGGAGTAGTA (SEQ ID NO: 66) | CGGTAAATGTGGTCGAGGAT (SEQ ID NO: 67) |
| GATA4 | CCCGACACCCCAATCTC (SEQ ID NO: 68) | CAGGCGTTGCACAGATAGTG (SEQ ID NO: 69) |
| GATA6 | CCAACTTCCACCTCTTCTAACTCAG (SEQ ID NO: 70) | TCTTGACCCGAATACTTGAGCTC (SEQ ID NO: 71) |
| ATF5 | CTATGAGGTCCTTGGGGGAG (SEQ ID NO: 72) | CTCGCTCAGTCATCCAGTCA (SEQ ID NO: 73) |
| USF1 | ACAGTTGGAGAAAATCGGCA (SEQ ID NO: 74) | ATCCGAGGAACTGGTCCTTT (SEQ ID NO: 75) |
| USF2 | TTGATGGAACCAGAACACCC (SEQ ID NO: 76) | AGCTGGACGATCCAGTTGTT (SEQ ID NO: 77) |
| XBP1 | GTGAGCTGGAACAGCAAGTG (SEQ ID NO: 78) | CCAAGCGCTGTCTTAACTC (SEQ ID NO: 79) |
| ZHX2 | GGTCTGGATGTACCGACTGC (SEQ ID NO: 80) | AAAATTGGAATGGCACCAAC (SEQ ID NO: 81) |
| NFIA | ACCCCATCACATAGGGGTTT (SEQ ID NO: 82) | TAATGTCAGCGTCACTTGGC (SEQ ID NO: 83) |
| PXR | TTGCCCATCGAGGACCAGAT (SEQ ID NO: 84) | GTCTCCGCGTTGAACACTGT (SEQ ID NO: 85) |
| CAR | GTCCCACCTGCCCCTTTG (SEQ ID NO: 86) | AGTGGCGCCTCTGAGTCTTG (SEQ ID NO: 87) |
| FXR | CAGGATTTCAGACTTTGGACCAT (SEQ ID NO: 88) | CTTCAACCGCAGACCCTTTC (SEQ ID NO: 89) |
| PPARA | AGAGATTTCGCAATCCATCGG (SEQ ID NO: 90) | ACTGGTATTCCGTAAAGCCAAAG (SEQ ID NO: 91) |
| AHR | ACATCACCTACGCCAGTCG (SEQ ID NO: 92) | CGCTTGGAAGGATTTGACTTGA (SEQ ID NO: 93) |
| PPARG | TACTGTCGGTTTCAGAAATGCC (SEQ ID NO: 94) | GTCAGCGGACTCTGGATTCAG (SEQ ID NO: 95) |
| PPARD | GTGATCCACGACATCGAGACA (SEQ ID NO: 96) | TGCACGCTGATCTCCTTGTAG (SEQ ID NO: 97) |
| LXRA | CCTTCAGAACCCACAGAGATCC (SEQ ID NO: 98) | ACGCTGCATAGCTCGTTCC (SEQ ID NO: 99) |
| VDR | TCTCCAATCTGGATCTGAGTGAA (SEQ ID NO: 100) | ACAGCTCTAGGGTCACAGAAG (SEQ ID NO: 101) |
| GR | CCAACGGTGGCAATGTGAAAT (SEQ ID NO: 102) | CCAAGGACTCTCATTCGTCTCT (SEQ ID NO: 103) |
| CYP2E1 | CTGACCACCCTCCGGAACTAT (SEQ ID NO: 104) | GGCCTTGGGTCTTCCTGAGT (SEQ ID NO: 105) |

TABLE 3-continued

Primers used for qRT-PCR, Related to FIG. 3

| Gene | Forward Primer (5'→3') | Reverse Primer (5'→3') |
|---|---|---|
| CYP2D6 | GTGTCCAACAGGAGATCGACG (SEQ ID NO: 106) | CACCTCATGAATCACGGCAGT (SEQ ID NO: 107) |
| CYP2C19 | GAAGAGGAGCATTGAGGACCG (SEQ ID NO: 108) | GCCCAGGATGAAAGTGGGAT (SEQ ID NO: 109) |
| CYP2C9 | GCCACATGCCCTACACAGATG (SEQ ID NO: 110) | TAATGTCACAGGTCACTGCATGG (SEQ ID NO: 111) |
| CYP1A2 | CTTCGTAAACCAGTGGCAGG (SEQ ID NO: 112) | AGGGCTTGTTAATGGCAGTG (SEQ ID NO: 113) |
| CYP3A4 | AGCCTGGTGCTCCTCTATCT (SEQ ID NO: 114) | CCCTTATGGTAGGACAAAAT (SEQ ID NO: 115) |
| CYP2B6 | CCGGGGATATGGTGTGATCTT (SEQ ID NO: 116) | CCGAAGTCCCTCATAGTGGTC (SEQ ID NO: 117) |
| CYP2A6 | GAGTTCCTGTCACTGTTGCG (SEQ ID NO: 118) | GTCCTGGCAGGTGTTTCATC (SEQ ID NO: 119) |
| UGT1A1 | CCATCATGCCCAATATGGTT (SEQ ID NO: 120) | CCACAATTCCATGTTCTCCA (SEQ ID NO: 121) |
| UGT1A3 | GCCAACAGGAAGCCACTATC (SEQ ID NO: 122) | CAGCAATTGCCATAGCTTTC (SEQ ID NO: 123) |
| UGT1A4 | AACGGGAAGCCACTATCTCA (SEQ ID NO: 124) | TCAGCAATTGCCATAGCTTTC (SEQ ID NO: 125) |
| UGT1A6 | AATTTCCTAAAGGCCGGTCA (SEQ ID NO: 126) | TTGATCCCAAAGAGAAAACCA (SEQ ID NO: 127) |
| UGT1A9 | ACTATCCCAAACCCGTGATG (SEQ ID NO: 128) | ACCACAATTCCATGTTCTCCA (SEQ ID NO: 129) |
| UGT2B7 | AACGTAATTGCATCAGCCCT (SEQ ID NO: 130) | GGTCATTCTGGGGTATCCAC (SEQ ID NO: 131) |
| UGT2B15 | GTTTTCTCTGGGGTCGATGA (SEQ ID NO: 132) | ATTTGGCTTCTTGCCATCAA (SEQ ID NO: 133) |
| NAT2 | CAGCCTAGTTCCTGGTTGCT (SEQ ID NO: 134) | GGATCTGGTGCTCAAGAATG (SEQ ID NO: 135) |
| BCRP | CTGAGATCCTGAGCCTTTGG (SEQ ID NO: 136) | AAGCCATTGGTGTTTCCTTG (SEQ ID NO: 137) |
| OATP1B1 | TTCAATCATGGACCAAAATCAA (SEQ ID NO: 138) | TGAGTGACAGAGCTGCCAAG (SEQ ID NO: 139) |
| OATP1B3 | GAAAACAAGACGCTGCAATG (SEQ ID NO: 140) | TCCTTTCTATTTGAGTGATGGAAA (SEQ ID NO: 141) |
| NTCP | AGGGGGACATGAACCTCAG (SEQ ID NO: 142) | AGGTCCCCATCATAGATCCC (SEQ ID NO: 143) |
| GAPDH | TGCACCACCAACTGCTTAGC (SEQ ID NO: 144) | GGCATGGACTGTGGTCATGAG (SEQ ID NO: 145) |

Primer for 18s rRNA was purchased from QIAGEN. Quantified values were normalized against the input determined by two housekeeping genes (GAPDH or RRN18S). For the positive control in qRT-PCR, five different batches of fresh isolated primary human hepatocytes were collected in RNAprotect (Qiagen) and stored at −20° C. Total RNA was isolated and then reverse-transcribed to cDNA as described above. Equal volumes of cDNA obtained from five different batches of freshly isolated primary human hepatocytes were mixed to be taken as the positive control.

Immunofluorescence and Flow Cytometric Analysis

Cells or tissue sections were fixed in 4% paraformaldehyde (Dingguo) at room temperature for 15 minutes and blocked with PBS containing 0.25% Triton X-100 and 5% normal donkey serum (Jackson ImmunoResearch Laboratories, Inc) at room temperature for 1 hour or at 4° C. overnight. Samples were incubated with primary antibodies at 4° C. overnight, washed three times with PBS and then incubated with appropriate secondary antibodies for 1 hour at room temperature in the dark. Nuclei were stained with DAPI (Roche). Experiments were repeated for three times and typical results were shown. The primary antibodies used for immuno-fluorescence are as follows: rabbit anti CYP3A4, rabbit anti CYP2C9, rabbit anti YP1A2, rabbit anti CYP2E1, rabbit anti CYP2D6 (all from AbD Serotec), Goat anti ALB (Bethyl Laboratories, INC), Rabbit anti NR5A2/LRH1 (Abcam), Rabbit anti COL1A1 (Abcam), Mouse anti E-CAD (Abcam), Mouse anti human nuclei (Millipore). The secondary antibodies used for immunofluorescence are as follows: DyLight® 550 Donkey anti rabbit and DyLight® 550 Donkey anti goat (from Abcam), DyLight 488 donkey anti goat Dylight 549 donkey anti goat, DyLight 488 donkey anti mouse, Dylight 549 donkey anti mouse, DyLight 488 donkey anti rabbit, Dylight 549 donkey anti rabbit (all from Jackson ImmunoResearch Laboratories). Flow cytometric assays were conducted as reported previously (Zhao et al., Cell Res., 23:157-161 (2013)).

RNA-Sequence Analysis

Total RNA was isolated from HEFs, HepG2 cells, ES-Heps, hiHeps and freshly isolated primary human hepatocytes. RNA sequencing libraries were prepared with the Illumina TruSeq RNA Sample Preparation Kit. The fragmented and randomly primed 200-bp paired-end libraries were sequenced on Illumina HiSeq 2000 sequencing system.

Toxicity Assays.

hiHeps were incubated with various concentrations of compounds dissolved in culture medium for 24 h. Cell viability was measured by MTT assay (Invitrogen) following the manufacturer's instructions and as described previously (Khetani and Bhatia, Nat Biotechnol 26, 120-126 (2008)).

Animals and Transplantation

Tet-uPA/Rag2$^{-/-}$/γc$^{-/-}$ mice on a BALB/c background were purchased from Beijing Vitalstar Biotechnology. hiHeps, ES-Heps, and primary human hepatocytes (2×10$^6$ cells/animal) were injected into the spleens of the mice. Blood samples were collected and human ALBUMIN was quantified using the Human Albumin ELISA Quantitation kit (Bethyl Laboratories). Livers of recipient mice were embedded in OCT compound (Sakura) and then frozen in liquid nitrogen. Cryostat sections (10 mm) were stained.

Statistical Analysis

For statistical analysis, a two-tailed unpaired t test was used. Results are expressed as mean±SD. p values are as follows: *p<0.05; p<0.01; *p<0.001.

Accession Numbers

RNA-sequencing data have been deposited in the NCBI Gene Expression Omnibus database under accession number GSE54066.

Results

Identification of Factors that Induce Hepatic Fate

To identify the combination of transcription factors that induce human embryonic fibroblasts (HEFs) into hepatocytes, a pool of transcription factors (Table 4) that were previously shown to be expressed in human hepatocytes and are crucial to the determination of hepatic cell fate was selected (Nagaoka and Duncan, Prog. Mol. Biol Transl Sci., 97:79-101 (2010); Zaret, Nat. Rev. Genet., 9:329-340 (2008)).

TABLE 4

Transcription Factors Analyzed in Freshly Isolated Primary Human Hepatocyte

| Gene | GeneBank Accession |
| --- | --- |
| FOXA1 | NM_004496 |
| FOXA2 | NM_021784 |
| PROX1 | NM_001270616 |
| CEBPA | NM_004364 |
| HNF1A | NM_000545 |
| HNF4A | NM_178849 |

TABLE 4-continued

Transcription Factors Analyzed in Freshly Isolated Primary Human Hepatocyte

| Gene | GeneBank Accession |
| --- | --- |
| HNF6 | NM_004498 |
| GATA6 | NM_005257 |
| PPARA | NM_005036 |
| ZHX2 | NM_014943 |
| LRH1 | NM_205860 |
| ONECUT2 | NM_004852 |
| ATF5 | NM_001193646 |
| USF2 | NM_003367 |
| USF1 | NM_007122 |
| ZGPAT | NM_032527 |
| NF1A | NM_001134673 |

Previous studies also showed that proliferation arrest and cell death are general barriers to cell reprogramming (Huang et al., Nature, 475:386-389 (2011); Zhao et al., Cell Stem Cell, 3:475-479 (2008)). Thus, MYC was employed in the reprogramming process, as well as p53 small interfering RNA (siRNA) was employed in the reprogramming process. Briefly, HNF1A and HNF4A are preferentially considered because of their critical role in both embryonic and adult liver among the 17 transcription factors. Then additional factors were screened using a "2+1" strategy by the addition of one candidate factor at a time to the combination of HNF1A and HNF4A.

The data showed that HNF6, cooperating with HNF4A and HNF1A, can result in a high percentage of Albumin (ALB)-positive cells within 20 days (data not shown). These three factor induced hepatocyte-like cells (3H cells) exhibited some hepatic properties, including glycogen synthesis and low-density lipoprotein (LDL) uptake (data not shown). However, the expression level of ALB in these cells was extremely low (FIG. 1A). Moreover, the expression of the major cytochrome P450 enzymes in hepatocytes was not detected in these cells (data not shown). Therefore, the 3H cells appear to be functionally immature, implying that additional factors are required for their full maturation.

Identification of Factors that Generate Mature Hepatocytes

To identify the factors capable of inducing the functional maturation of hepatocyte-like cells, a global gene expression analysis was performed on 3H cells, freshly isolated primary human hepatocytes (F-HEPs), and fetal liver cells. Differential expression of several hepatic transcription factors, including CEBPA, ATF5, and PROX1, was observed among the three samples (data not shown). These three genes were expressed at relatively low levels in the 3H cells and in fetal hepatocytes compared to the levels in adult hepatocytes. This difference was further confirmed by quantitative PCR (FIGS. 1B and 1C). Among these genes, PROX1 was shown in a recent study to be a key transcription factor that is critical in the metabolic maturation of hepatocytes (Zhao et al., Cell Res., 23:157-161 (2013)). CEBPA and ATF5 are highly abundant liver-enriched transcription factors, indicating the importance of transcriptional regulation in hepatic function. Furthermore, a gene expression study showed that these three genes were highly expressed in F-HEPs (FIG. 1D). Collectively, these data showed that overexpressing these factors can lead to the functional maturation of 3H cells.

Figure 1F:
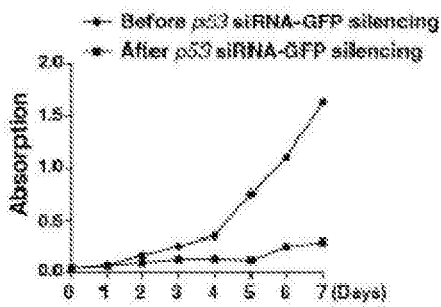
FIG. 1 F shows determination of the proliferation rate of the induced cells at different stages. Upper panel: MTT assay. Day 0 is set as the day when the induced cells were transferred to HCM (before p53 siRNA-GFP silence) or modified WEM (after p53 siRNA-GFP silence). Lower panel: Calculation of doubling time of the induced cells at the expansion stage (before p53 siRNA-GFP silence). Td, doubling time.
FIG. 1G is a bar graph showing a quantitative analysis of ALBUMIN expression among hiHeps, HEFs, and F-HEPs.
FIGS. 1H and 1I show reprogramming efficiency measured by flow cytometry analysis marked by ALB and AAT. n=3. APC, allophycocyanin.
FIG. 1J is a bar graph showing a quantitative analysis of Albumin secretion among hiHeps, HEFs, and F-HEPs by ELISA. n=3.
FIG. 1K shows the effect on the expression of hepatic functional genes after removal of individual factors detected by qRT-PCR. n=2. Data are presented as mean+/−s.d.
Figure 1G:
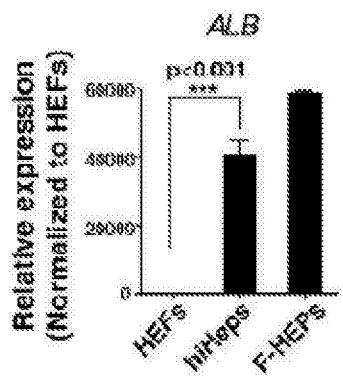
Figure 1H:
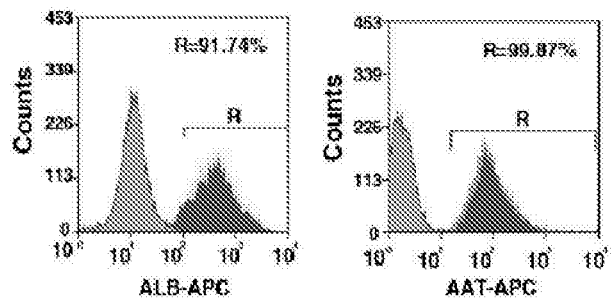
Figure 1I:
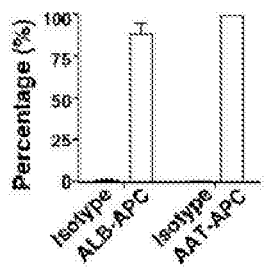
Figure 1J:
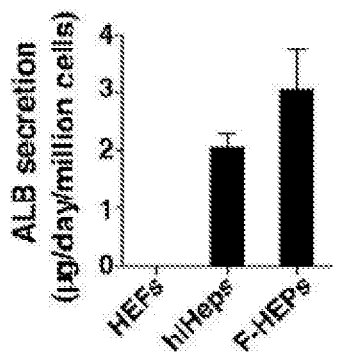
Figure 1K:
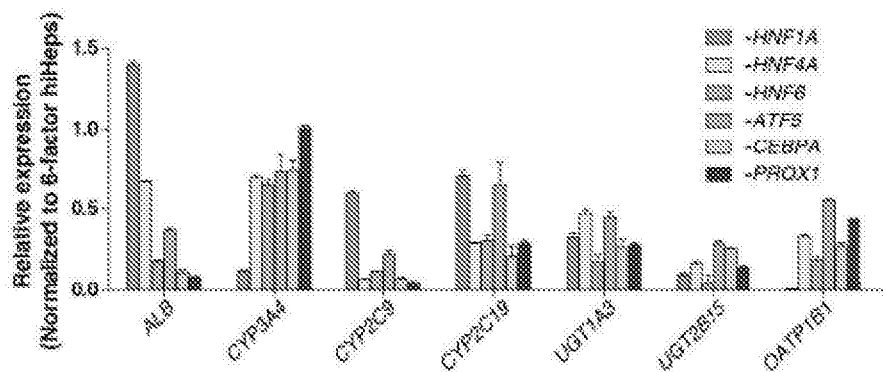

To generate mature human hepatocytes from fibroblasts, the three factors with CEBPA, PROX1, and ATF5, were combined, and overexpressed in HEFs following the scheme shown in FIG. 1E. A dramatic morphological change of fibroblasts into epithelial cells was observed in 1 week. These cells proliferated rapidly in hepatocyte culture medium (HCM), with the doubling time ranging from 9 to 11 hr (FIG. 1F). At 2 weeks post infection, the replated cells showed the typical morphology of primary human hepatocytes (data not shown). At about 25 days postinfection, p53 siRNA was silenced, as indicated by a GFP reporter (data not shown), and the induced cells were transferred to a modified William's E medium (FIGS. 1E and 1F). Quantitative PCR results showed that the induced hepatocyte-like cells expressed ALB at a level that was comparable to that of primary human hepatocytes (FIG. 1G), which was significantly higher than that of 3H cells (FIG. 1A). The reprogramming efficiency was further analyzed and found that 90% of the induced cells were ALB positive and nearly 100% were α-1 antitrypsin (AAT) positive (FIGS. 1H and 1I). The secretion of ALB was dramatically enhanced and was comparable to that of primary human hepatocytes (FIG. 1J). Furthermore, the four major cytochrome P450 enzymes, CYP3A4, CYP1A2, CYP2C9, and CYP2C19, were also expressed in the induced cells as detected by immunostaining (data not shown). Removal of any of these six factors would lead to a substantial decrease in the expression of drug metabolic enzymes and transporters (FIG. 1K). These results indicate that functional hepatic properties were obtained in these induced hepatocyte-like cells, which were termed hiHeps.

hiHeps Possess the Typical Characteristics of Human Hepatocytes

To evaluate hepatic fate conversion, typical hepatic features were first analyzed. Immunofluorescence microscopy showed that the epithelial marker E-cadherin (ECAD) was coexpressed with ALB in hiHeps (data not shown). In addition, the fibroblast marker COL1A1 was not detected (data not shown). These results indicate a successful mesenchymal-epithelial transition in hiHeps. Next, endogenous hepatic transcription network activation in hiHeps was further examined using RT-PCT.

The RT-PCR results showed that the endogenous expression of FOXA1, FOXA2, and FOXA3 (Zaret et al., *Nat. Rev. Genet.*, 9:329-340 (2008)) was activated in iHeps (FIG. 2A). LRH1, another core transcription factor involved in the hepatic cross-regulatory network (Nagaoka and Duncan, *Prog. Mol. Biol Transl Sci.*, 97:79-101 (2010)), was also endogenously expressed in hiHeps (FIG. 2A).

Figure 2C:
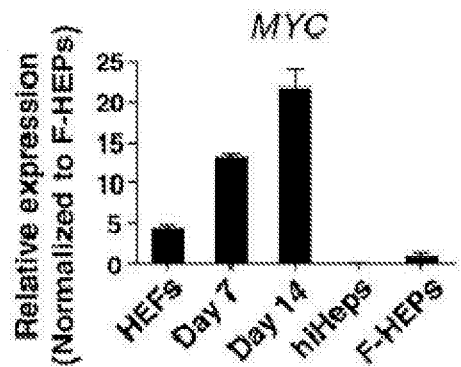
FIG. 2C shows relative expression of MYC during the hepatic conversion process measured by qRT-PCR. Day 7 and day 14, 7 and 14 days post infection. n=2.

The expression of FOXA2 and LRH1 was confirmed using immunofluorescence (data not shown). Additionally, fibroblast marker genes, including COL1A1, PDGFRB, and THY1, were not detected in hiHeps (FIG. 2A). In accordance with p53 siRNA silencing exogenous expression of HNF1A, HNF6, HNF4A, ATF5, PROX1, and CEBPA was silenced in hiHeps (FIG. 2B). The primers used in FIG. 2A can specifically identify endogenous transcripts of HNF1A, HNF4A, PROX1 and CEBPA. These primers are designed to bind to the unique 5'UTR or 3'UTR of endogenous transcripts rather than coding sequences. In addition, MYC was decreased in iHeps to a level lower than that of freshly isolated primary human hepatocytes, as revealed by quantitative RT-PCR (qRT-PCR) (FIG. 2C). Collectively, these data indicate that hiHeps gain a hepatic transcription network.

Next, hiHeps was evaluated for functional characteristics of human hepatocytes. hiHeps were competent for LDL uptake (data not shown). In addition, hiHeps could incorporate indocyanine green (ICG) from the medium and exclude the absorbed ICG after withdrawal (data not shown). Oil red O staining in hiHeps showed an accumulation of fatty droplets, and Periodic Acid-Schiff (PAS) staining indicated glycogen synthesis (data not shown). Similar to human adult hepatocytes, hiHeps were AFP negative (data not shown). G banding analysis revealed that hiHeps had a normal karyotype after 7 weeks of culture (data not shown). Besides HEFs, similar results were obtained when adult foreskin fibroblasts were converted as described herein using the same factors (data not shown). Collectively, these results indicate that hiHeps exhibit typical hepatic functional features.

The global gene expression patterns in hiHeps and F-HEPs were compared by RNA sequencing. Principle component analysis and hierarchical clustering analysis revealed that hiHeps established from different donors were clustered with human hepatocytes and separated from human fibroblasts, HepG2 cells, and human embryonic stem cell (ESC)-derived hepatocytes (ES-Heps) (data not shown). Indeed, hepatic transcription factors were upregulated (As it is depicted in FIG. 2A, these factors are FOXA1, FOXA2, FOXA3, CEBPA, HNF1A, HNF4A, PROX1 and LRH1) and the expression of fibroblast signature genes (As it is depicted in FIG. 2A, these factors are PDGFB1, THY1 and COL1A1) was downregulated in hiHeps (data not shown). Additionally, hiHeps displayed the gene expression patterns of hepatocytes in a set of genes involved in lipoprotein, cholesterol, fat, glucose, and drug metabolism (data not shown). Altogether, these results indicate that hiHeps show a similar expression profile to primary human hepatocytes.

Establishment of the Central Network of Drug Metabolism in hiHeps

Figure 3A:
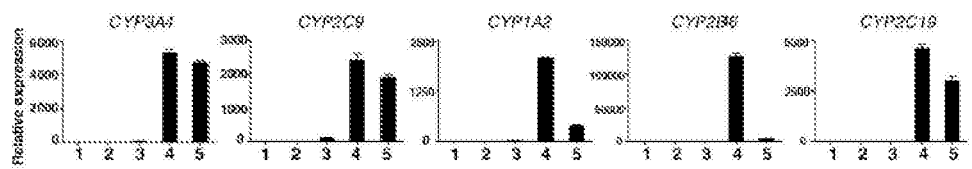
FIGS. 3A-3C show a quantitative analysis of the expression of drug metabolic phase I (FIG. 3A) and phase II enzymes (FIG. 3B) and phase III transporters (FIG. 3C) in HEFs, HepG2 cells, ES-Heps, hiHeps, and F-HEPs. The relative expression of each gene was normalized to HEFs; if not detected, it was normalized to HepG2 cells. n=2. 1=HEFs; 2=HepG2 cells; 3=ES-Heps; 4=hiHeps; 5=F-Heps.
Figure 3B:
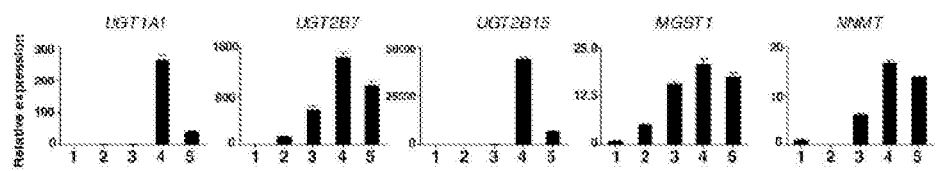
Figure 3C:
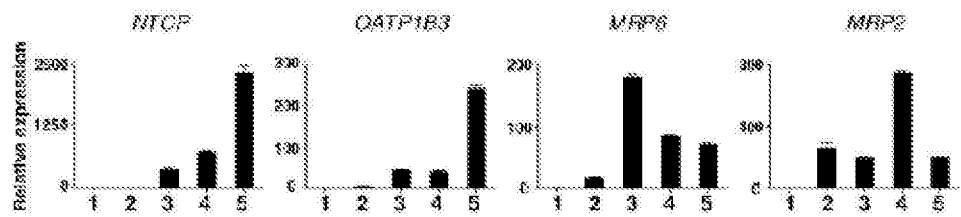
Figure 3D:
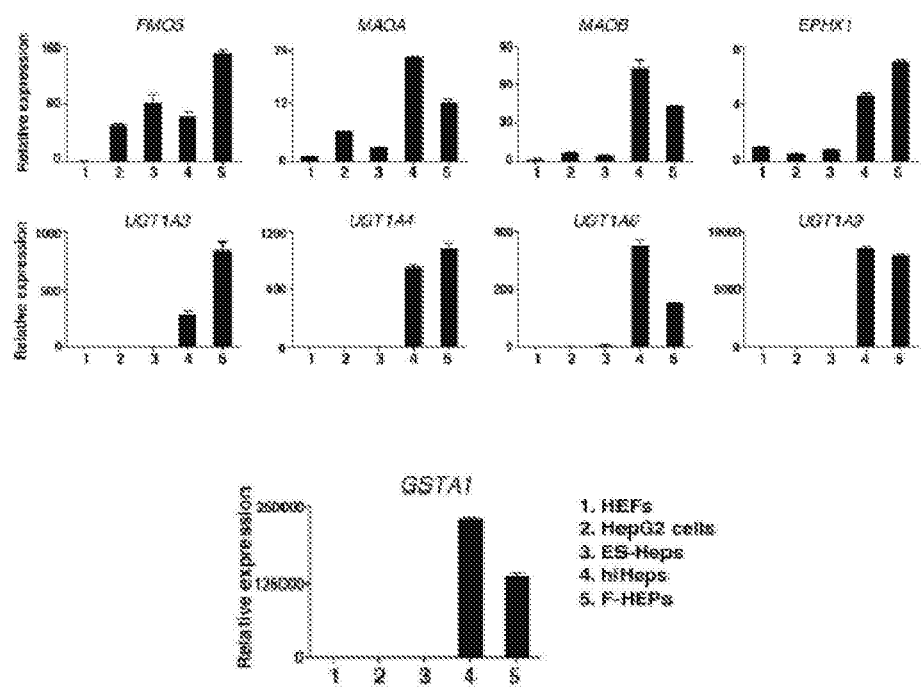
FIG. 3D is a bar graph showing quantitative analysis of the expression of drug metabolic Phase II enzymes and Phase III transporters in HEFs, HepG2 cells, ES-Heps, hiHeps and F-HEPs. The relative expression for each gene was normalized to HEFs; if not detected, normalized to HepG2 cells. n=2.
Figure 3E:
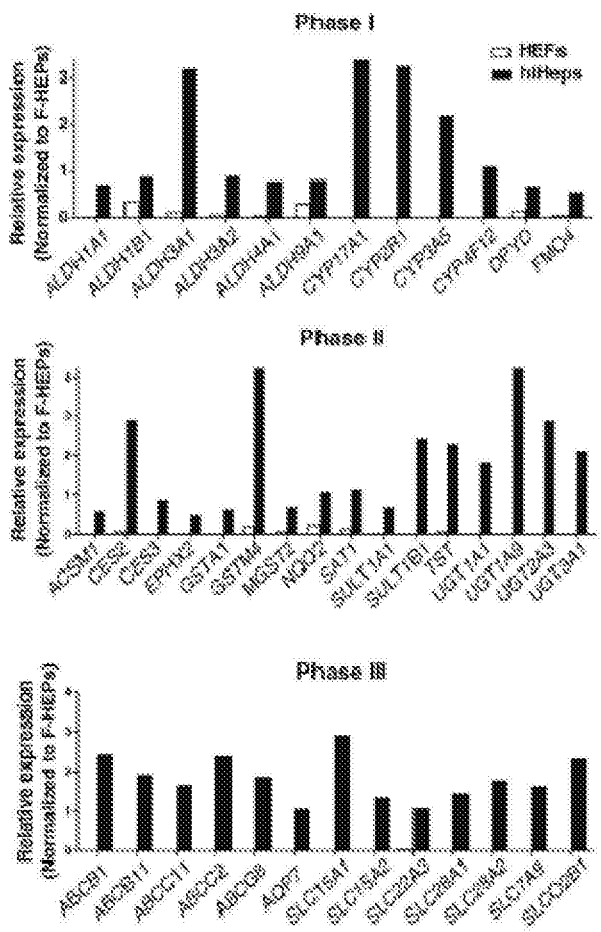
FIG. 3E is a bar graph showing quantitative comparison of phase I, phase II, phase III mRNA in hiHeps and HEFs to F-HEPs.

To evaluate whether hiHeps expressed key enzymes in drug metabolism, the expression in hiHeps of five key CYP enzymes, CYP1A2, CYP2B6, CYP2C9, CYP2C19, and CYP3A4 in hiHeps was quantitatively confirmed. The five key CYPs are major phase I enzymes that account for 60% of human drug oxidation (Zhou et al., *Drug Metab. Rev.*, 41:89-295 (2009)). As the positive control, pooled F-HEPs from five individual donors were used. Notably, comparable mRNA levels of these major CYPs could be detected in hiHeps and F-HEPs, in contrast to their expression in hepatocytes derived from human ESCs and HepG2 cells (FIG. 3A). Next, hiHeps were analyzed for the presence of phase II enzymes and phase III transporters, which are important for the excretion of xenobiotic drugs. The expression levels of these genes were similar to those in F-HEPs (FIGS. 3B-3D). Additionally, hiHeps expressed a broad spectrum of phase I and phase II metabolic enzymes and phase III transporters (FIG. 3E). Collectively, these findings show that the central network of drug metabolism was successfully established in hiHeps and resembled that of pooled freshly isolated primary human hepatocytes.

Figure 4A:
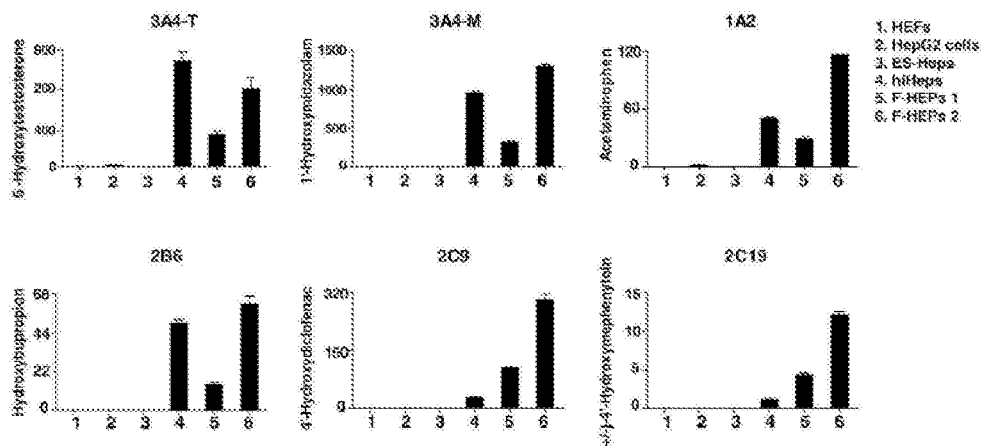
FIG. 4A shows the metabolic activities of CYP3A4 (3A4-T, testosterone; 3A4-M, midazolam), CYP1A2 (phenacetin), CYP2B6 (bupropion), CYP2C9 (diclofenac), and CYP2C19 [(S)-mephenytoin] in hiHeps, ES-Heps, F-HEPs1, F-HEPs2, HepG2 cells, and HEFs as determined by HPLC-MS. n=3. Two batches of freshly isolated primary human hepatocytes (F-HEPs1 and F-HEPs2) were applied as the positive control. The results are presented as pmol/min per million cells. Data are presented as mean±SD.

Level of Key Drug Metabolic Activities in hiHeps is Comparable to that in Freshly Isolated Primary Human Hepatocytes To evaluate the drug metabolic activities of hiHeps, the studies first focused on CYP3A4. Using ultraperformance liquid chromatography-tandem mass spectrometry technology, the drug metabolic activity of CYP3A4 in hiHeps was detected by using two structurally different substrates, testosterone and midazolam. Because of the remarkable interindividual variability in drug clearance, two batches of freshly isolated primary human hepatocytes were used as the positive control. In contrast to the HepG2 cell line, ES-Heps, and HEFs, hiHeps were able to metabolize the two CYP3A4-selective substrates efficiently and the metabolism efficiency is comparable to the metabolism seen with freshly isolated hepatocytes (F-HEPs) (FIG. 4A). Zhao, et al. disclose that ES-Heps express CYP3A4 with activities at levels that are lower than those seen in 25-week-old fetal hepatocytes and human adult primary hepatocytes (Zhao, et al., *Cell Res.*, 23:157-161 (2013)). Furthermore, the metabolic activities of CYP1A2 and CYP2B6 in hiHeps were found to be comparable to that of F-HEPs (FIG. 4A). The activities of CYP2C9 and CYP2C19 in hiHeps were approximately 30% of F-HEPs (FIG. 4A). The metabolic activities of all these CYP enzymes in hiHeps were at least 100-fold higher than that of ES-Heps. These data indicate that hiHeps exhibit comparable metabolic activities of the key CYP enzymes to those of freshly isolated primary human hepatocytes.

Figure 3F:
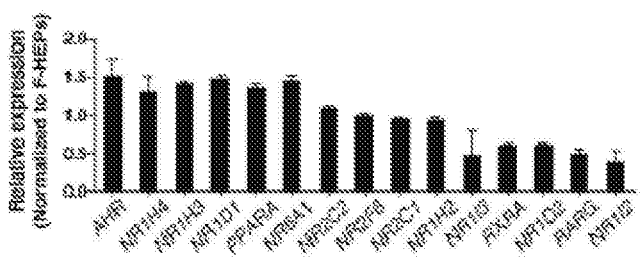
FIG. 3F is a bar graph showing quantitative comparison of nuclear receptors mRNA in hiHeps to F-HEPs.
Figure 4B:
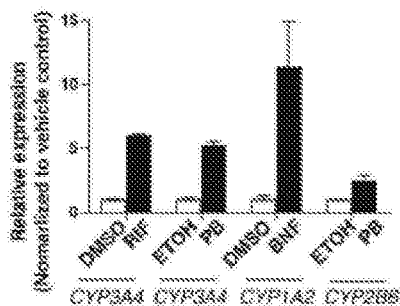
FIG. 4B is a bar graph showing quantitative analysis of the fold-induction of the CYP3A4, CYP1A2 and CYP2B6 in hiHeps treated with different inducers. n=2. Rif, Rifampin; PB, Phenobarbital; ETOH, Ethanol; BNF, β-Naphthoflavone.

To further evaluate the functional central network of drug metabolism in hiHeps, the expression of nuclear receptors between hiHeps and F-HEPs, which are critical in regulating the expression of metabolizing enzymes, was compared. Nuclear receptors that are responsible for the xenobiotic metabolizing system were expressed in hiHeps (FIG. 3F). Moreover, hiHeps responded to the standard inducers of CYP3A4, CYP1A2, and CYP2B6 at the mRNA level (FIG. 4B). Taken together, these data show a functional establishment of the nuclear receptor network in hiHeps.

To assess the potential application of hiHeps in studying hepatotoxicity, acute toxicity of model hepatotoxins were quantified. As hepatotoxicity is the most common adverse event resulting in drug failure (Sahi et al., *Curr. Drug Discov. Technol.*, 7:188-198 2010), the sensitivity of drug toxicity is a key index for the potential application of human hepatocytes in drug discovery. hiHeps showed a level of sensitivity comparable to that of primary human hepatocytes when incubated with a series of model hepatotoxins (FIG. 4C), showing the potential of using hiHeps for testing drug toxicity.

Repopulation of Tet-uPA/Rag2$^{-/-}$γc$^{-/-}$ Mouse Liver with hiHeps

Figure 4C:
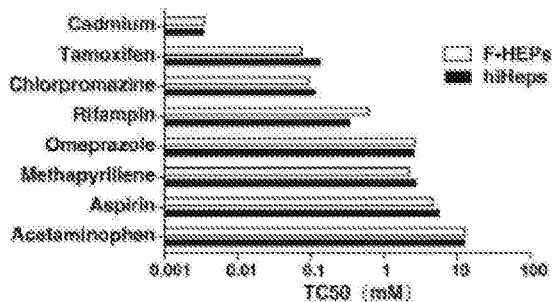
FIG. 4C is a bar graph showing an analysis of the sensitivity of hiHeps to multiple model hepatotoxins. F-HEPs were used as the positive control. Data are presented as mean. n=3.
Figure 5A:
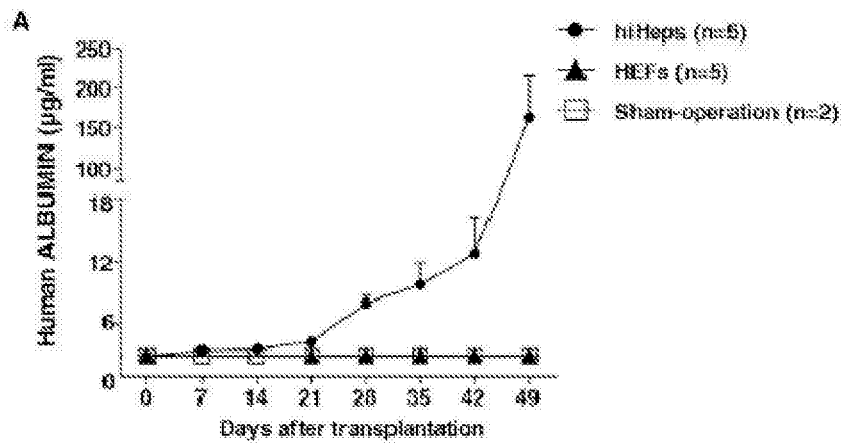
FIG. 5A is a line graph showing the level of human albumin in mouse serum was monitored by ELISA.
Figure 5B:
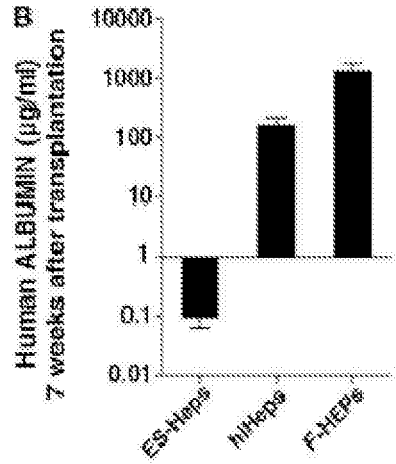
FIG. 5 B is a bar graph comparing human ALB secretion in mouse serum among ES-Heps (n=16), hiHeps (n=5), and F-HEPs (n=6).
FIG. 5C shows flow cytometry analysis of the engraftment efficiencies of hiHeps. Mouse 1 and mouse 2 secreted human ALB at 267 and 313 ug/ml, respectively. HN, human nuclei; PE, phycoerythrin.
Figure 5C:
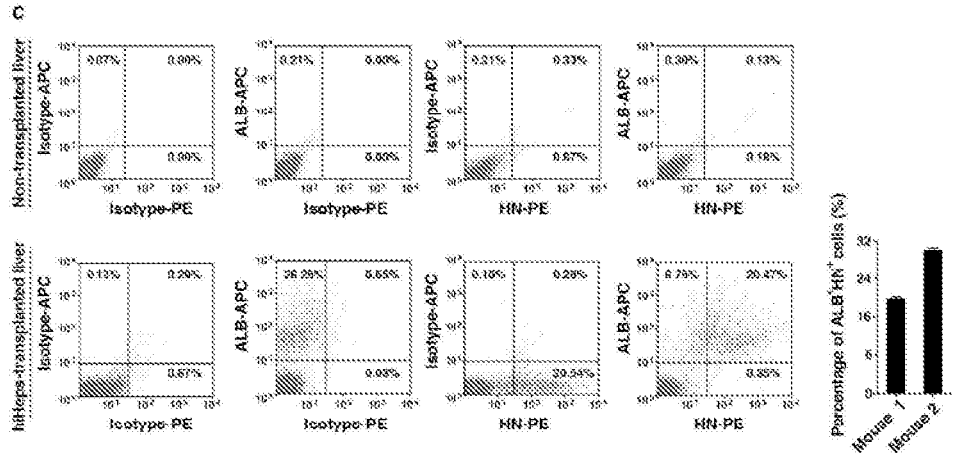

To investigate the capacity of hiHeps to repopulate mouse liver, Tet-uPA (urokinase-type plasminogen activator)/Rag2$^{-/-}$/γc$^{-/-}$ mice were injected intrasplenically with hiHeps (Song et al., *Am. J. Pathol.*, 175:1975-1983 (2009)). The secretion of human Albumin in mouse serum increased gradually and the highest level reached was 313 mg/ml at 7 weeks after hiHep transplantation (FIGS. 5A-5C), which was 1,000-fold higher than ES-Heps and comparable to primary human hepatocytes (FIG. 5B). To analyze the engraftment efficiency, hepatocytes were isolated from whole liver of two mice and measured by flow cytometry analysis. The repopulation efficiency was about 30% in the mouse that secreted 313 mg/ml human Albumin (FIG. 4C). No tumorigenesis was observed 2 months after hiHep transplantation. Grafts of hiHeps were also analyzed. Six weeks after transplantation, clusters of cells expressing human ALB were observed in the recipient mice (data not shown). To confirm the metabolic function of hiHeps in vivo, CYP expression was analyzed. The expression of major CYPs including CYP3A4, CYP2C9, CYP1A2, CYP2E1, CYP2C19, and CYP2D6 (data not shown) indicated that hiHeps can be functional in vivo. Collectively, these results show that hiHeps can robustly repopulate the liver of Tet-uPA/Rag2$^{-/-}$/γc$^{-/-}$ mice and were functional in vivo.

Discussion

These studies show that human hiHeps are readily and reproducibly generated from HEFs using a combination of hepatic fate conversion factors HNF1A, HNF4A, and HNF6 together with the maturation factors ATF5, PROX1, and CEBPA. Similar to primary human hepatocytes, hiHeps exhibit many typical hepatic features, including their epithelial morphology, expression of hepatocyte specific markers, basic functional properties of hepatocytes, and global gene expression patterns. Importantly, an integral spectrum of phase I and phase II drug-metabolizing enzymes and phase III drug transporters is well established in hiHeps. Furthermore, transplanted hiHeps can repopulate up to 30% of the livers of Tet-uPA/Rag2$^{-/-}$/γc$^{-/-}$ mice and secrete more than 300 mg/ml human albumin in vivo. This data shows that human hepatocytes with drug-metabolizing functions can be generated from fibroblasts using lineage reprogramming. One key question in lineage reprogramming is how to obtain fully functional cells. In hepatic transdifferentiation, mouse induced hepatocyte-like cells were generated with several important hepatic characteristics, through the expression of hepatic fate determination factors in fibroblasts (Huang et al., 2011; Sekiya and Suzuki, *Nature*, 475:390-393 (2011)). However, incomplete hepatocyte differentiation and expression of certain hepatoblast markers by hiHeps are compatible with an immature or progenitor-like state (Willenbring, *Cell Stem Cell*, 9:89-91 (2011)). These studies also show that that certain hepatic fate determination factors could reprogram HEFs into hepatocyte-like cells. However, these cells are not functional until the addition of three additional factors (FIGS. 1G-1J). The additional three factors promote further metabolic maturation of hiHeps (data not shown). Thus, hepatic fate determination and hepatic functional maturation may be governed by different master genes and are somewhat independent of each other. To obtain fully functional cells, the ectopic expression of cell fate determination factors may not be sufficient, and additional functional maturation factors are required to promote this process.

The drug metabolic capacity of human hepatocytes is one of the most important functions that distinguish hepatocytes from other lineages and has broad applications in drug development. Efforts to differentiate human pluripotent stem cells into hepatocytes have resulted in cells that were functionally immature. A recent study showed that human ES-Heps express CYP1A2 and CYP3A4 (Zhao et al., *Cell Res.*, 23:157-161 (2013)). However, the activities of these two CYP enzymes were significantly lower than that of primary hepatocytes. In another study, differentiated hepatocytes exhibited CYP3A4 and CYP1A2 activities only comparable to that of cultured primary hepatocytes (Ogawa et al., *Development*, 140:3285-3296 2013). However, a number of liver-essential functions were progressively lost with time in cultured primary hepatocytes (Elaut et al., *Curr. Drug Metab.* 7:629-660 (2006)). In the studies disclosed herein, the gold standard, freshly isolated primary human hepatocytes, was used as the positive control. The hiHeps disclosed herein express the key phase I (CYP3A4, CYP2C9, CYP2C19, CYP2B6, and CYP1A2) and phase II drug-metabolizing enzymes and phase III drug transporters at a level comparable to that of freshly isolated primary human hepatocytes. Importantly, the metabolic activities of the five CYP enzymes in hiHeps were comparable to those in freshly isolated primary human hepatocytes, indicating the potential application of hiHeps in evaluating drugs metabolized by these CYP enzymes (FIG. 4A). The expression of endogenous nuclear receptors related to xenobiotic metabolizing systems was also detected in these cells (Nakata et al., *Drug Metab. Pharmacokinet.*, 21:437-457 (2006)) (FIG. 3F). Moreover, the expression of CYP3A4, CYP1A2, and CYP2B6 was increased by the standard inducers (FIG. 4B). In addition, because integrated metabolism pathways (phase I and phase II enzymes and phase III drug transporters) in hepatocytes are of vital importance for drug discovery (Castell et al., *Expert Opin. Drug Metab.*

Toxicol. 2:183-212 (2006)), the drug metabolic network of hiHeps was closely analyzed. The expression pattern of genes encoding the drug metabolizing markers was similar to that in primary human hepatocytes, implying an upregulation of the drug metabolic network in hiHeps (FIGS. 3A-3F). Collectively, these results indicate the integral establishment of the central network of functional drug metabolism in hiHeps, making these cells a potential alternative for preclinical screening assays.

Figure 4D:
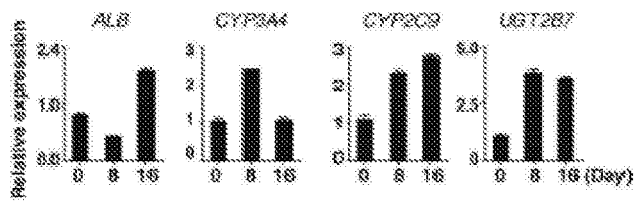
FIG. 4D is a bar graph showing gene expression analysis of hepatic genes after hiHeps formation by qRT-PCR. The relative expression was normalized to that of day 0. Data are presented as mean+/−s.d.

Another key characteristic of human hepatocytes in drug development is their sensitivity to drug toxicity. Human hepatocytes derived from human pluripotent stem cells have a relatively low sensitivity to drug toxicity (Zhao et al., *Cell Res.,* 23:157-161 (2013)). By contrast, the sensitivity of hiHeps disclosed herein to multiple model hepatotoxins is comparable to that of primary human hepatocytes (FIG. 4C). Thus, hiHeps can be a valuable alternative cell resource in hepatotoxicity assays for new drug discovery. Importantly, our results demonstrate that the induced cells could be expanded at a large scale at an early stage (FIG. 1F), and the function of hiHeps could be maintained for 16 days (FIG. 4D). Considering the reprogramming efficiency (FIGS. 1H and 1I), more than 1011 functional hi-Heps can be obtained starting from 104 of fibroblasts (data not shown). These results show that hiHeps could be used in a practical manner for pharmaceutical development.

Hepatocyte transplantation is a promising alternative to orthotopic liver transplantation (Dhawan et al., *Nat Rev Gastroenterol Hepatol,* 7:288-298 (2010)). However, the limited supply of donor organs that can provide good-quality cells remains a major challenge. In the studies described herein, hiHeps were able to repopulate mouse liver robustly and secreted up to 313 mg/ml human ALBUMIN, which is two orders of magnitude higher than recent studies using human hepatocytes derived from human embryonic stem cells (FIGS. 5A and 5B) (Takebe et al., *Nature,* 499:481-484 (2013); Woo et al., *Gastroenterology,* 142:602-611 (2012)). Furthermore, transplanted hiHeps expressed major CYP enzymes (data not shown), indicating that hiHeps retained drug metabolic capabilities in vivo. Collectively, hiHeps can serve as a potential cell source for the establishment of a humanized mouse model and hepatocyte transplantation.

In conclusion, human hepatocytes were generated with drug metabolizing functions using the combined expression of cell fate determination factors and cell maturation factors. The generation of functional human hepatocytes with lineage reprogramming provides a way to obtain well-characterized, reproducible, and functional human hepatocytes for pharmaceutical applications.

The invention claimed is:

1. A method for inducing human fibroblast cells into induced hepatocytes-like cells (iHeps), comprising the steps of:
   (a) introducing one or more nucleic acid sequences encoding six factors, wherein the six factors are Hepatocyte nuclear factor 1-alpha (HNF1A), Hepatocyte nuclear factor 4-alpha (HNF4A), Hepatocyte nuclear factor 6-alpha (HNF6), Activating transcription factor 5 (ATF5), Prospero homeobox protein (PROX1), and CCAAT/enhancer-binding protein alpha (CEBPA), into isolated fibroblasts;
   (b) culturing the cells from the step (a) in a somatic cell medium;
   (c) expanding the cells from the step (b) in a hepatocyte cell culture medium; and
   (d) culturing the cells from the step (c) in a hepatocyte maturation medium wherein expression of the six factors is effective to induce formation of iHeps, wherein the iHeps do not express α-fetoprotein, and wherein the iHeps secret albumin, and are capable of taking up LDL, incorporating indocyanine green (ICG), synthesizing and storing glycogen and accumulating fat.

2. The method of claim 1, wherein the step (a) further comprises treating the cells to upregulate MYC and downregulate p53.

3. The method of claim 2, wherein the step (a) comprises transfecting the cells with a vector expressing p53 siRNA and inhibiting the expression of p53 siRNA at the end of the step (c).

4. The method of claim 1, wherein in the step (a) the cells are transformed with nucleic acids as set forth by SEQ ID NOs: 1-7, respectively.

5. The method of claim 1, wherein in the step (b) the cells are cultured in the somatic cell culture medium for a period of at least 7 days.

6. The method of claim 1 wherein in the step (c) the cells are cultured in the hepatocyte cell culture medium for a period of about 15 to 30 days, preferably, 18-30 days, more preferably about 18 days.

7. The method of claim 1 wherein in the step (d) the cells are cultured in the hepatocyte maturation medium for a period of at least 5 days.

8. The method of claim 1, wherein the fibroblast cells are derived from a mammal, the method further comprising identifying iHeps by detecting the expression of at least one hepatic marker selected from the group consisting of albumin, Cytochrome P450 (CYP)3A4 and CYPB6, glycogen synthesis and storage, and/or fatty droplet accumulation.

9. The method of claim 8, wherein the mammal is selected from the group consisting of human, rat, mouse, monkey, dog, cat, cattle, rabbit, horse and pig.

10. The method of claim 1, wherein the iHeps express at least one drug metabolizing enzyme selected from the group consisting of CYP3A4, CYPB6, CYP1A2, CYP2C9, CYP2C19, or combinations thereof and optionally, wherein MYC expression level in the iHeps is lower than the MYC expression level found in hepatocytes obtained from the corresponding organism.

11. The method of claim 1, wherein the non-hepatocyte cells are fibroblast cells, and optionally wherein the iHeps express E-cadherin, the iHeps do not express one or more of the fibroblast marker genes selected from COL1A1, PDGFRB, THY1 and α-fetoprotein, or a combination thereof.

12. The method of claim 1, wherein the iHeps at least one drug metabolic phase II enzyme or phase II transporter selected from the group consisting of CYP1A2, CYP2C9, CYP2C19, UDP glucuronosyltransferase (UGT)1A1, UGT1A3, UGT1A4, UGT1A6, UGT1A9, GSTA1, UGT2B7, UGT2515, Microsomal glutathione-S-transferase 1 (MGST1), nicotinamide N-methyltransferase (NNMT), NTCP, organic anion-transporting polypeptide 1B3 (OATP1B3), Multidrug resistance protein(MRP)6, MRP2, Flavin-containing monooxygenase 5 (FMO5), Monoamine oxidase (MAO)A, MAOB, and epoxide hydrolase 1 (EPHX1).

13. The method of claim 1, wherein the metabolic activity of at least one of CYP3A4, CYPB6, CYP1A2, CYP2C9, and CYP2C19 is at least 50% higher than the activity of the same enzyme in ES-Heps (embryonic stem cell (ESC)-derived hepatocytes) obtained from the same organism.

14. The method of claim 13, wherein the metabolic activity of at least one of CYP3A4, CYPB6, CYP1A2, CYP2C9, and CYP2C19 is 55%, 60%, 65%, 70%, 75%, 80%, 85%, 90%, 95%, 100% or more, higher than the activity in ES-Heps.

15. The method of claim 13, wherein the metabolic activity of at least one of CYP3A4, CYPB6, CYP1A2, CYP2C9, and CYP2C19 is at least 100-fold higher than that of ES-Heps.

16. A method for inducing human fibroblast cells into induced hepatocytes-like cells (iHeps), comprising the steps of:
(a) introducing one or more nucleic acid sequences encoding HNF1A, HNF4A, HNF6, ATF5, PROX1, and CEBPA, into isolated human fibroblasts;
(b) culturing the cells from the step (a) in a somatic cell medium;
(c) expanding the cells from the step (b) in a hepatocyte cell culture medium; and
(d) culturing the cells from the step (c) in a hepatocyte maturation medium such that iHeps form, wherein the iHeps do not express α-fetoprotein, and wherein the iHeps secret albumin, and are capable of taking up LDL, incorporating indocyanine green (ICG), synthesizing and storing glycogen and accumulating fat;
the method further comprising identifying iHeps by detecting the expression of at least one hepatic marker selected from the group consisting of albumin, Cytochrome P450 (CYP)3A4 and CYPB6, glycogen synthesis and storage, and/or fat accumulation,
wherein the mammal is a human.

17. A method for inducing human fibroblast cells into induced hepatocytes-like cells (iHeps), comprising the steps of:
(a) introducing one or more nucleic acid sequences encoding HNF1A, HNF4A, HNF6, ATF5, PROX1, and CEBPA, into isolated human fibroblasts;
(b) culturing the cells from the step (a) in a somatic cell medium;
(c) expanding the cells from the step (b) in a hepatocyte cell culture medium; and
(d) culturing the cells from the step (c) in a hepatocyte maturation medium such that iHeps form, wherein the iHeps do not express α-fetoprotein, and wherein the iHeps secret albumin, and are capable of taking up LDL, incorporating indocyanine green (ICG), synthesizing and storing glycogen and accumulating fat.

* * * * *